(12) United States Patent
Kondo

(10) Patent No.: US 11,963,747 B2
(45) Date of Patent: Apr. 23, 2024

(54) BLOOD PRESSURE MEASUREMENT DEVICE

(71) Applicant: OMRON HEALTHCARE Co., Ltd., Kyoto (JP)

(72) Inventor: Katsunori Kondo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 783 days.

(21) Appl. No.: 16/951,699

(22) Filed: Nov. 18, 2020

(65) Prior Publication Data
US 2021/0068680 A1 Mar. 11, 2021

Related U.S. Application Data

(63) Continuation of application No. PCT/JP2019/020051, filed on May 21, 2019.

(30) Foreign Application Priority Data

May 24, 2018 (JP) ................................ 2018-099735

(51) Int. Cl.
*A61B 5/021* (2006.01)
*A61B 5/00* (2006.01)

(52) U.S. Cl.
CPC .......... *A61B 5/02141* (2013.01); *A61B 5/681* (2013.01); *A61B 5/6843* (2013.01)

(58) Field of Classification Search
CPC ... A61B 5/02141; A61B 5/681; A61B 5/6843; A61B 2562/0247; A61B 2562/046;
(Continued)

(56) References Cited

U.S. PATENT DOCUMENTS

| 4,947,855 A | 8/1990 | Yokoe et al. |
| 5,908,027 A * | 6/1999 | Butterfield ............. A61B 5/021 |
| | | 600/503 |

(Continued)

FOREIGN PATENT DOCUMENTS

| CN | 107613855 | 1/2018 |
| EP | 0 823 238 | 2/1998 |

(Continued)

OTHER PUBLICATIONS

International Preliminary Report on Patentability dated Nov. 26, 2020 in International (PCT) Application No. PCT/JP2019/020051.
(Continued)

*Primary Examiner* — Jacqueline Cheng
*Assistant Examiner* — Tho Q Tran
(74) *Attorney, Agent, or Firm* — Wenderoth, Lind & Ponack, L.L.P.

(57) ABSTRACT

A blood pressure measurement device having an attach portion including: an opening portion provided at a position opposite a region where one artery of a wrist is found and an end surface that curves conforming to a shape in a circumferential direction of a portion of the wrist; a fastener on the attach portion; and a sensing body including: a sensor unit opposite the opening portion, the sensor unit including a sensor module that comes into contact with the region where the one artery of the wrist is found and an air bag that presses the sensor module toward the wrist by expanding when the device is worn on the wrist, a case that houses the sensor module to allow the sensor module to move in one direction with respect to the opening portion, and a biasing member that biases the sensor module in a direction away from the wrist.

8 Claims, 29 Drawing Sheets

(58) Field of Classification Search
CPC . A61B 5/02233; A61B 5/0225; A61B 5/4893; A61B 5/6824; A61B 5/6831; A61B 5/02116; A61B 2560/0443
USPC .................................................. 16/291, 293
See application file for complete search history.

(56) References Cited

U.S. PATENT DOCUMENTS

| | | | |
|---|---|---|---|
| 2010/0185104 A1* | 7/2010 | Kim | A61B 5/02233 600/499 |
| 2018/0146871 A1 | 5/2018 | Ajima | |
| 2019/0046048 A1 | 2/2019 | Kitagawa et al. | |

FOREIGN PATENT DOCUMENTS

| | | |
|---|---|---|
| JP | H01-288228 A | 11/1989 |
| JP | 2017-42200 A | 3/2017 |
| JP | 2017-189467 A | 10/2017 |
| WO | 2017/179425 | 10/2017 |

OTHER PUBLICATIONS

Chinese Office Action dated Jun. 9, 2023 in corresponding Chinese Patent Application No. 201980028748.3, with English machine translation.

* cited by examiner

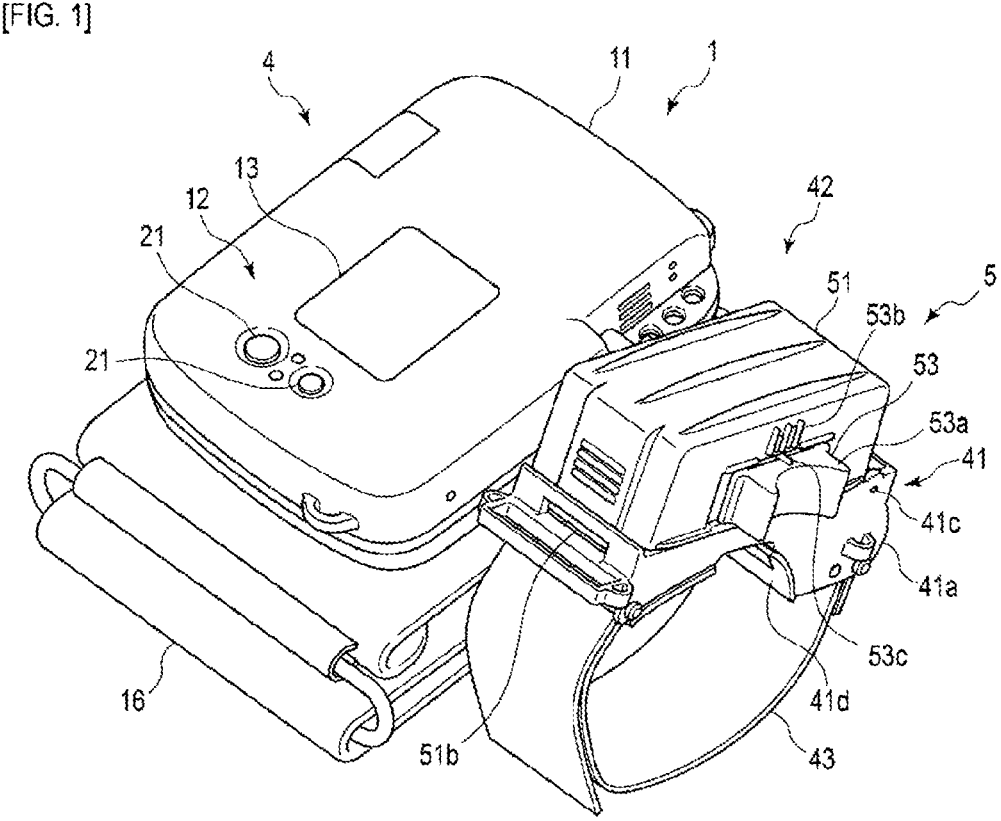
[FIG. 1]

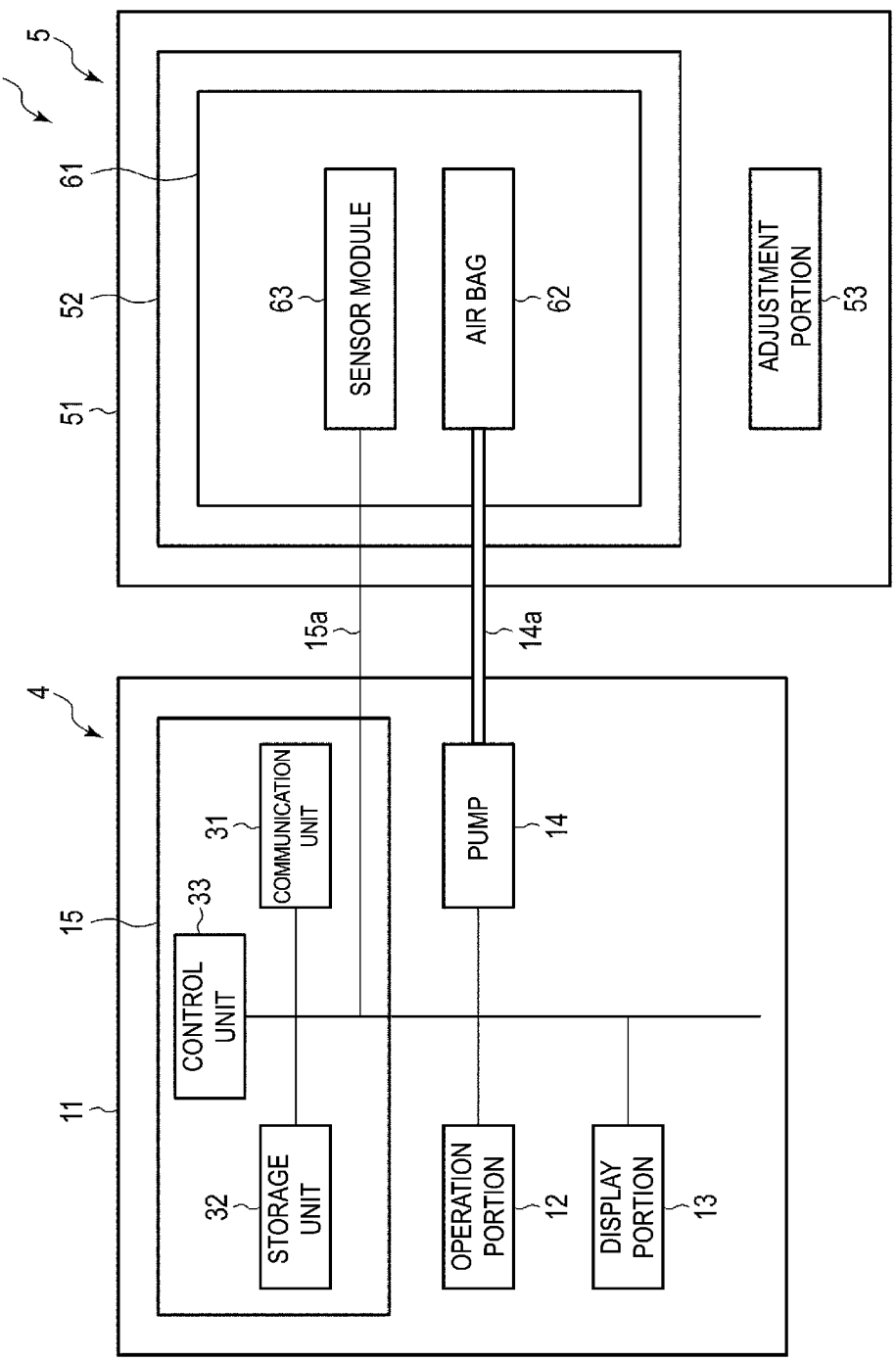

[FIG. 3]
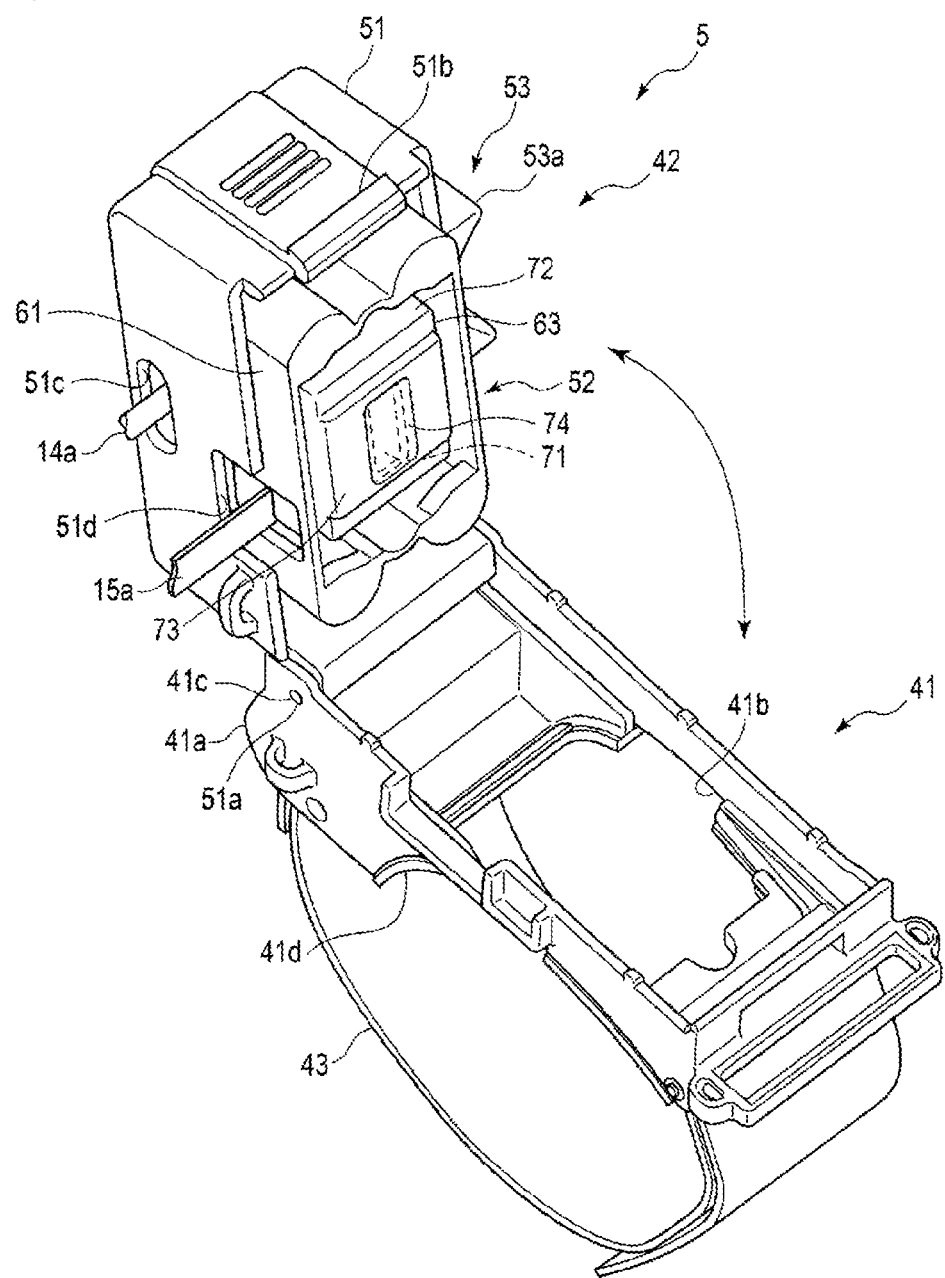

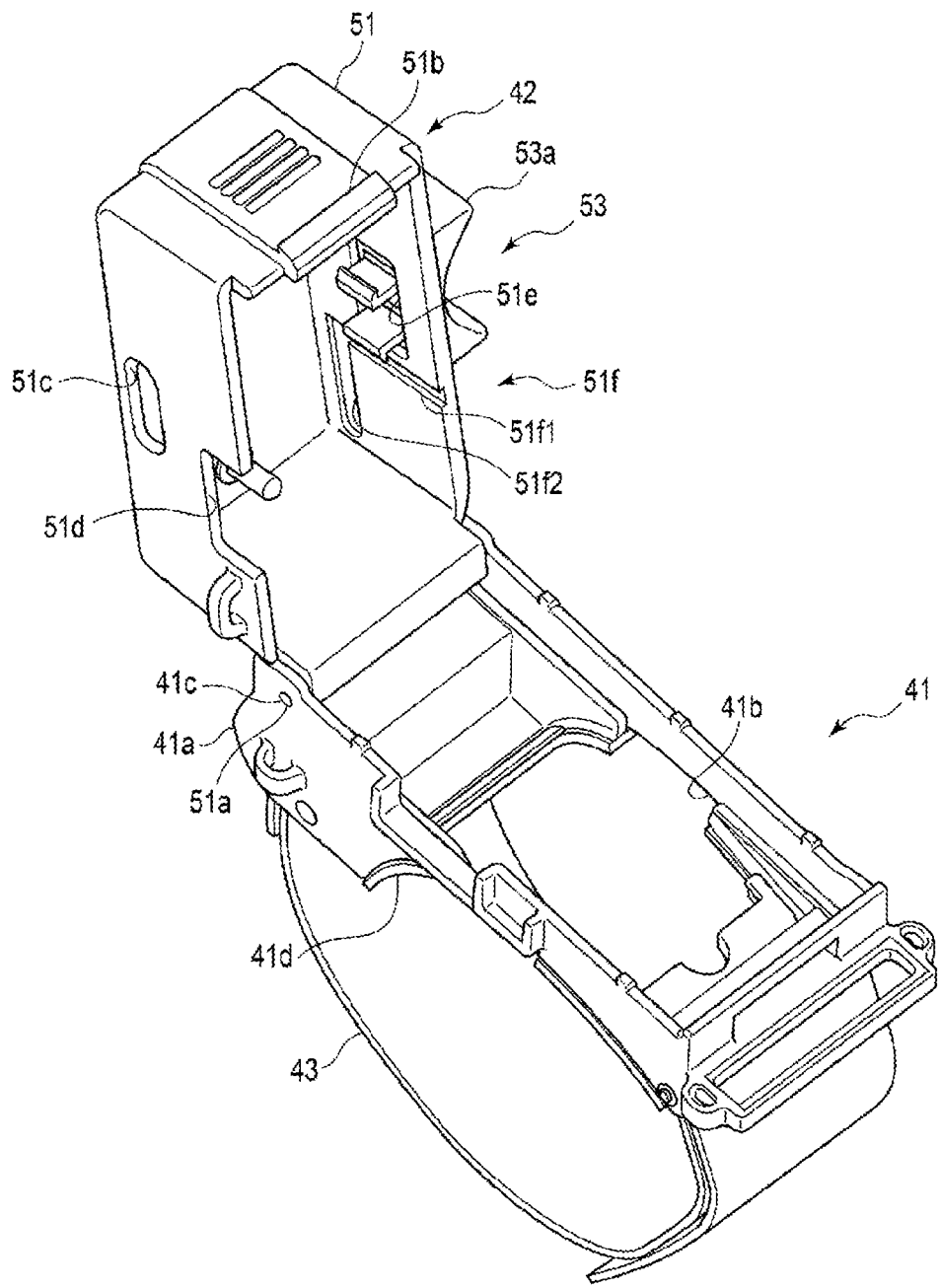

[FIG. 5]
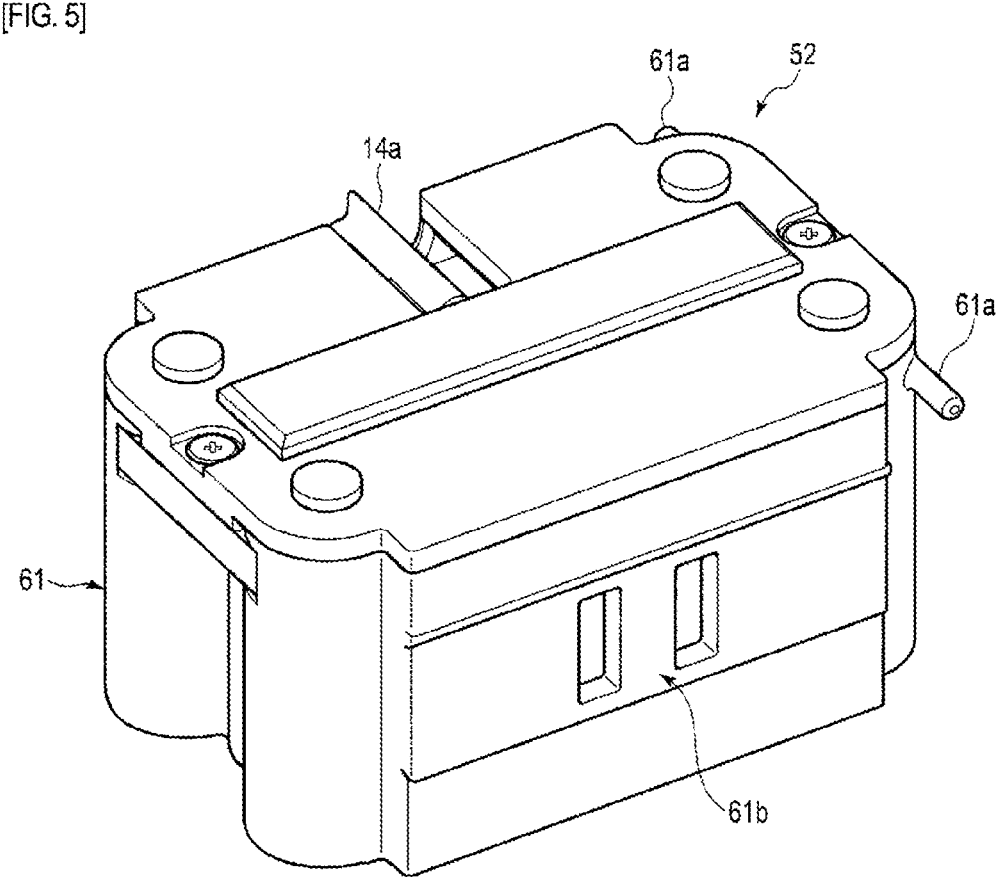

[FIG. 6]
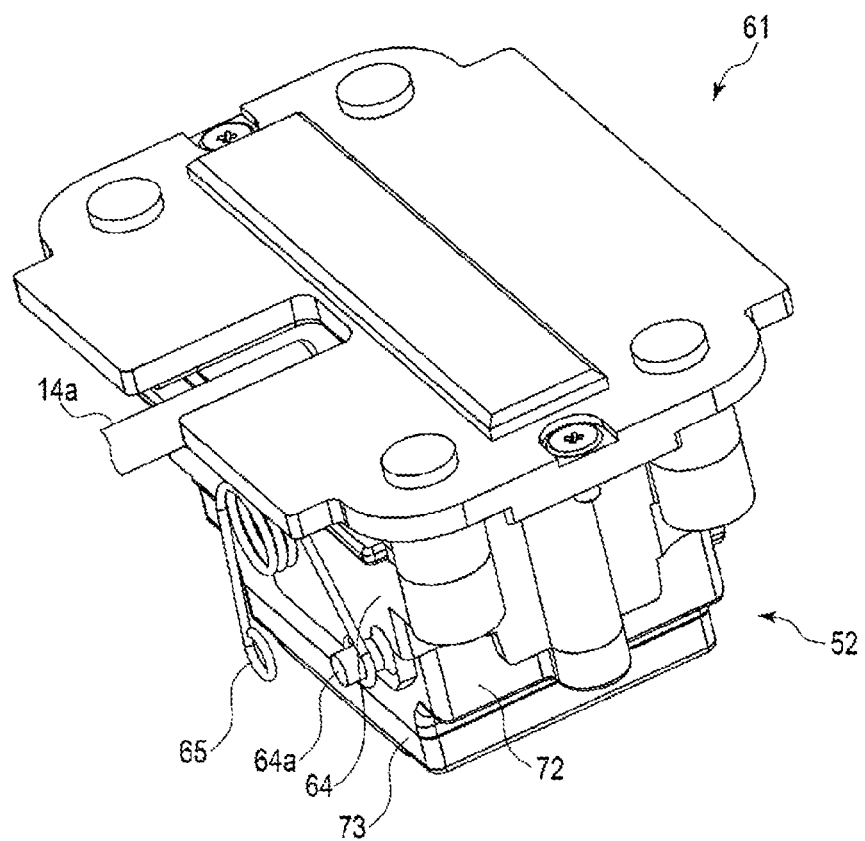

[FIG. 7]
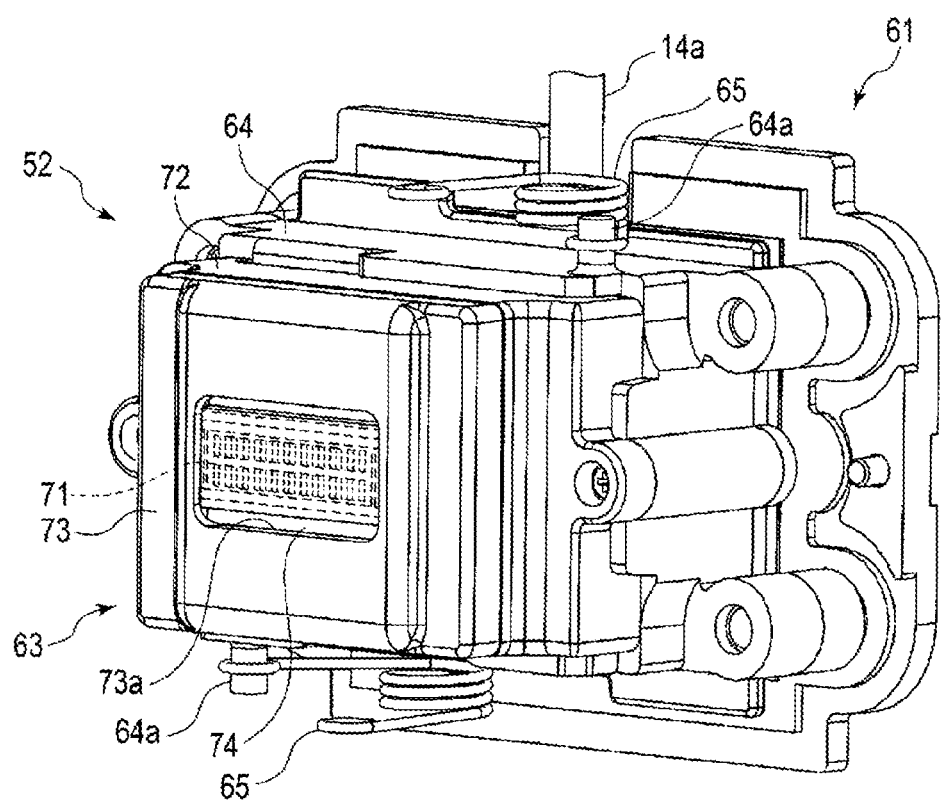

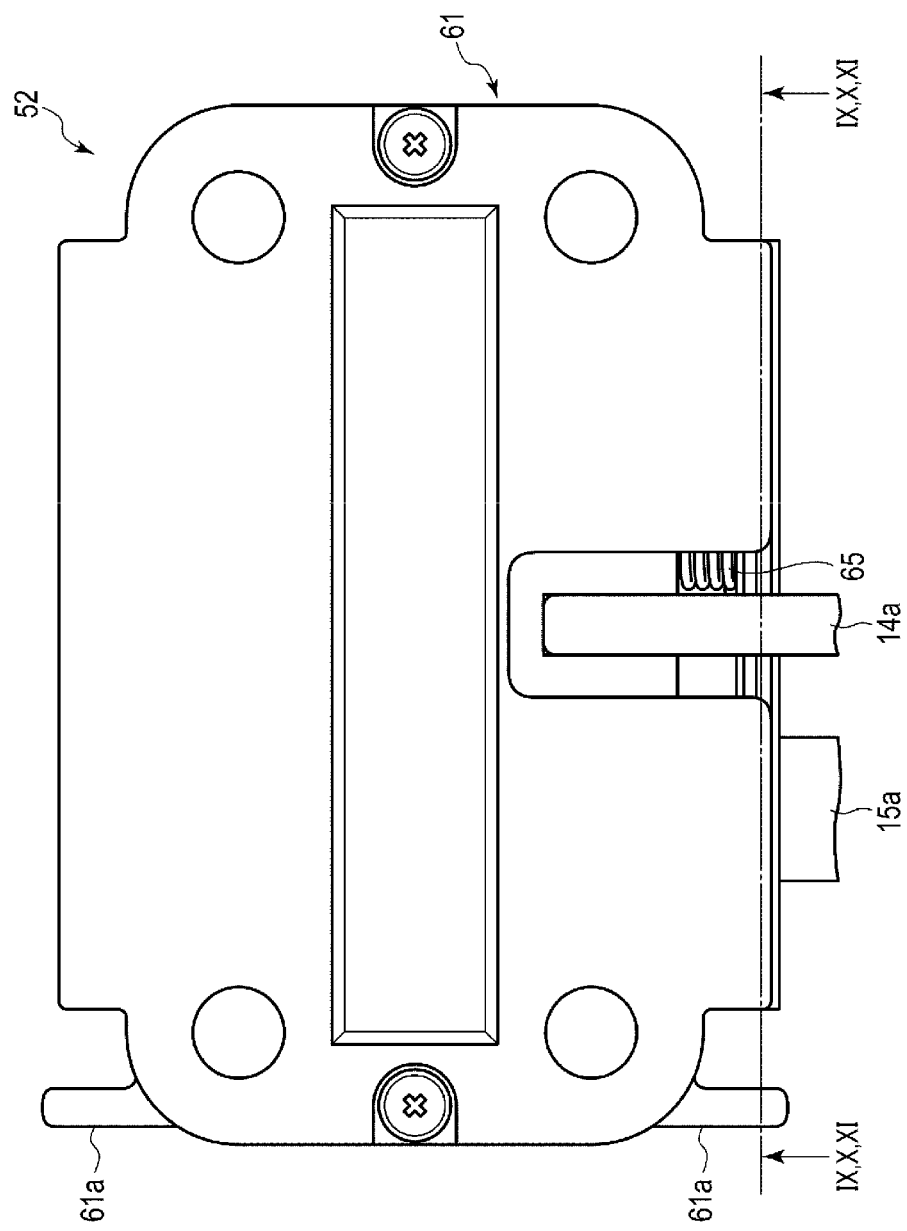

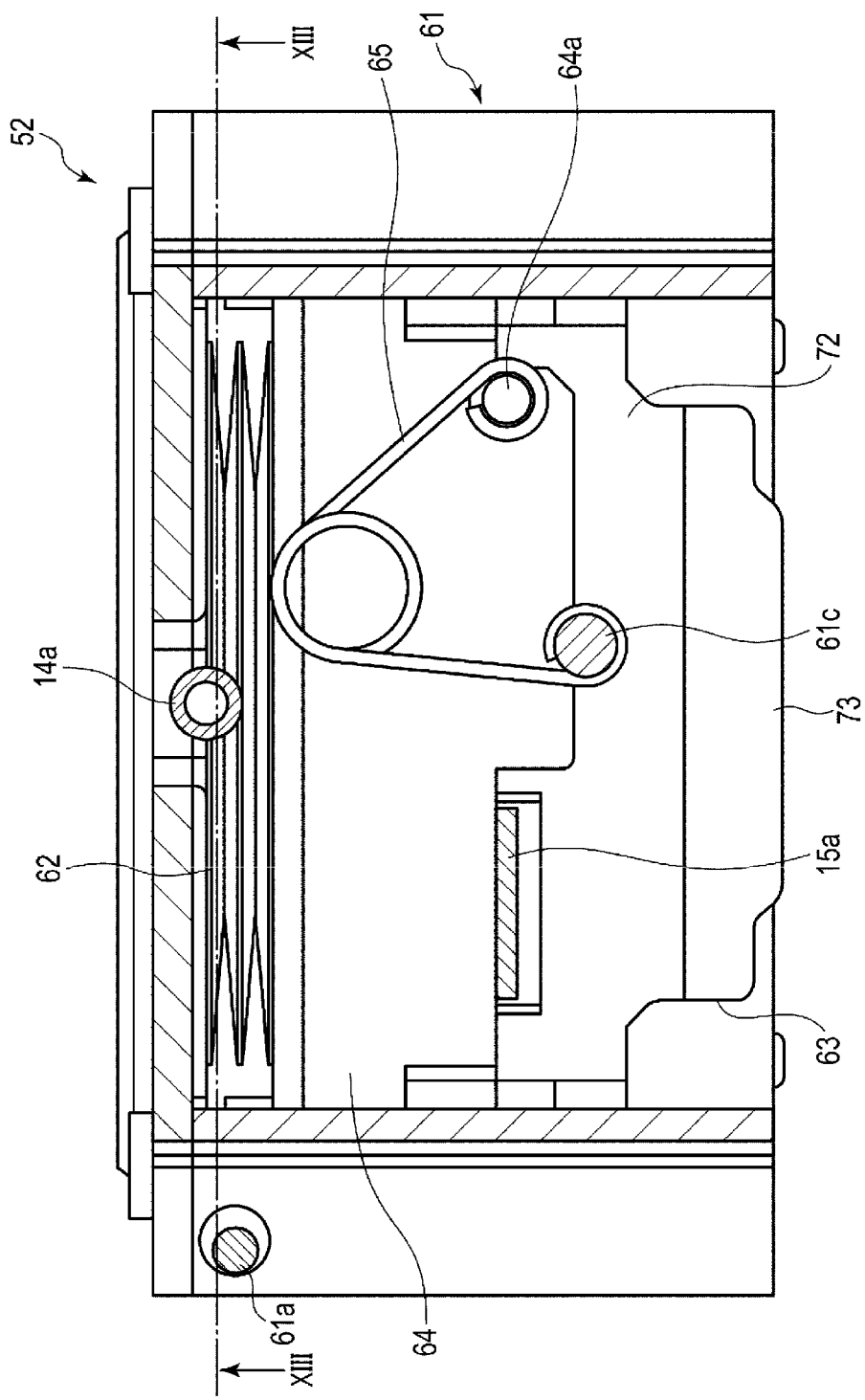

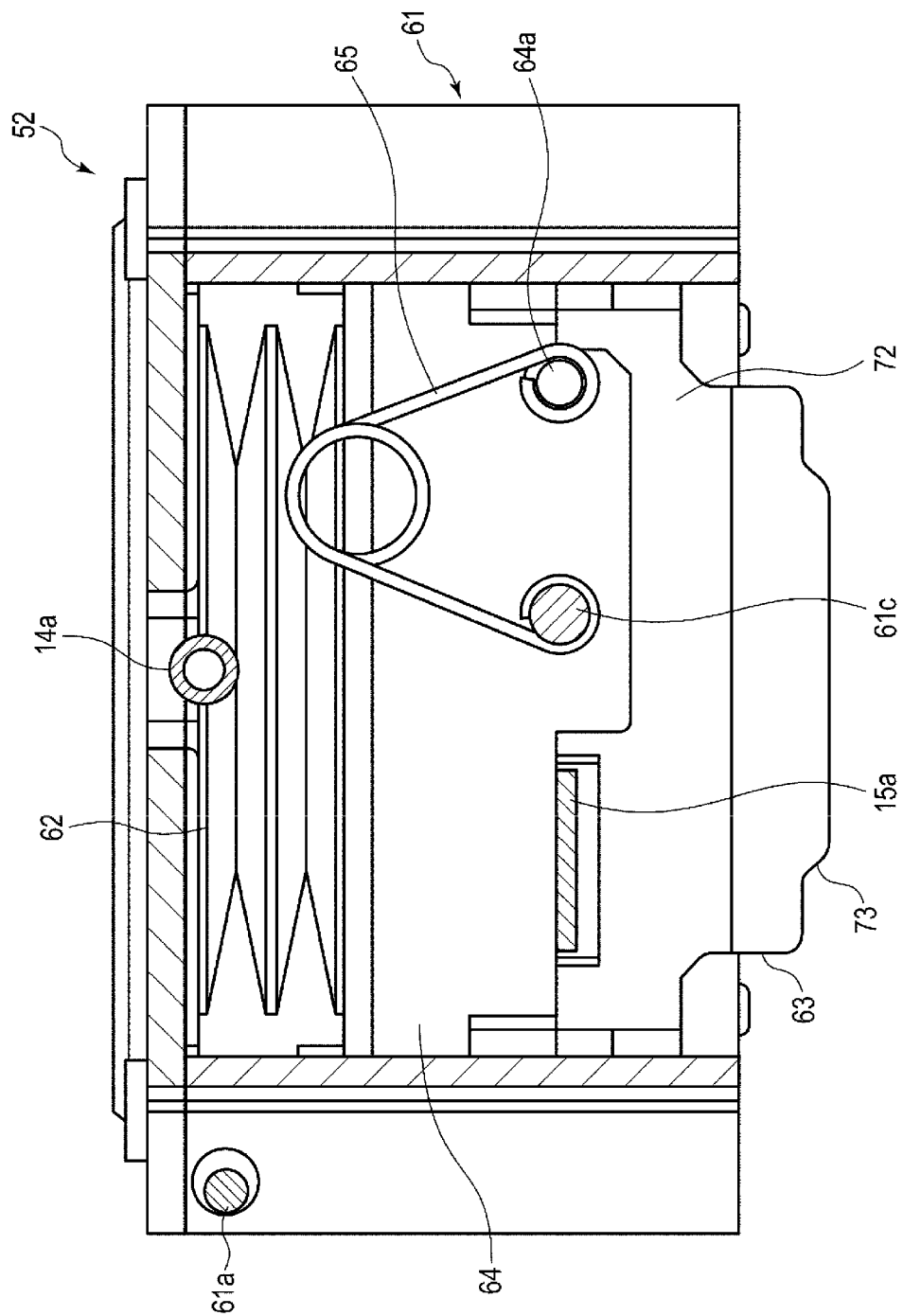

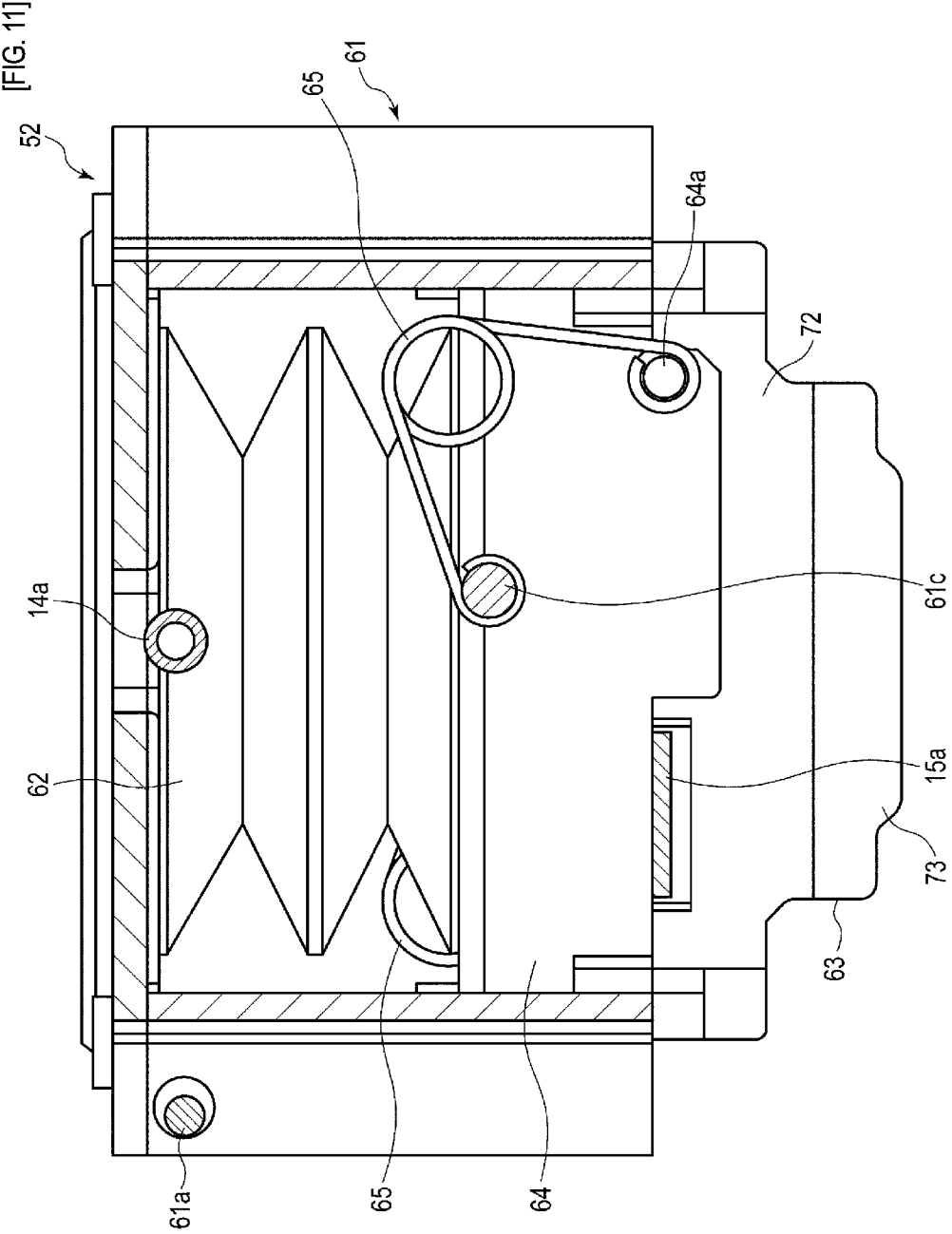

[FIG. 12]
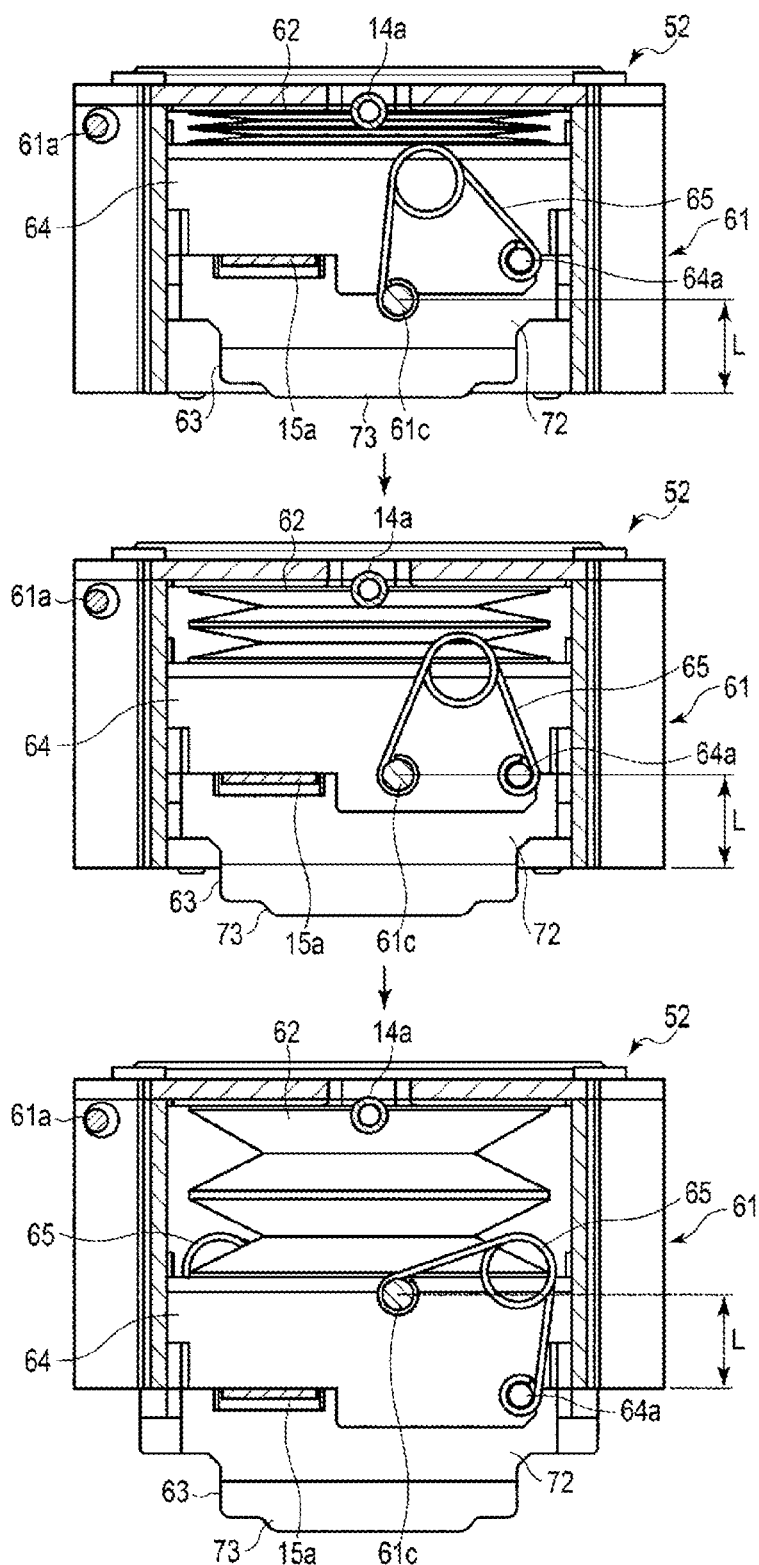

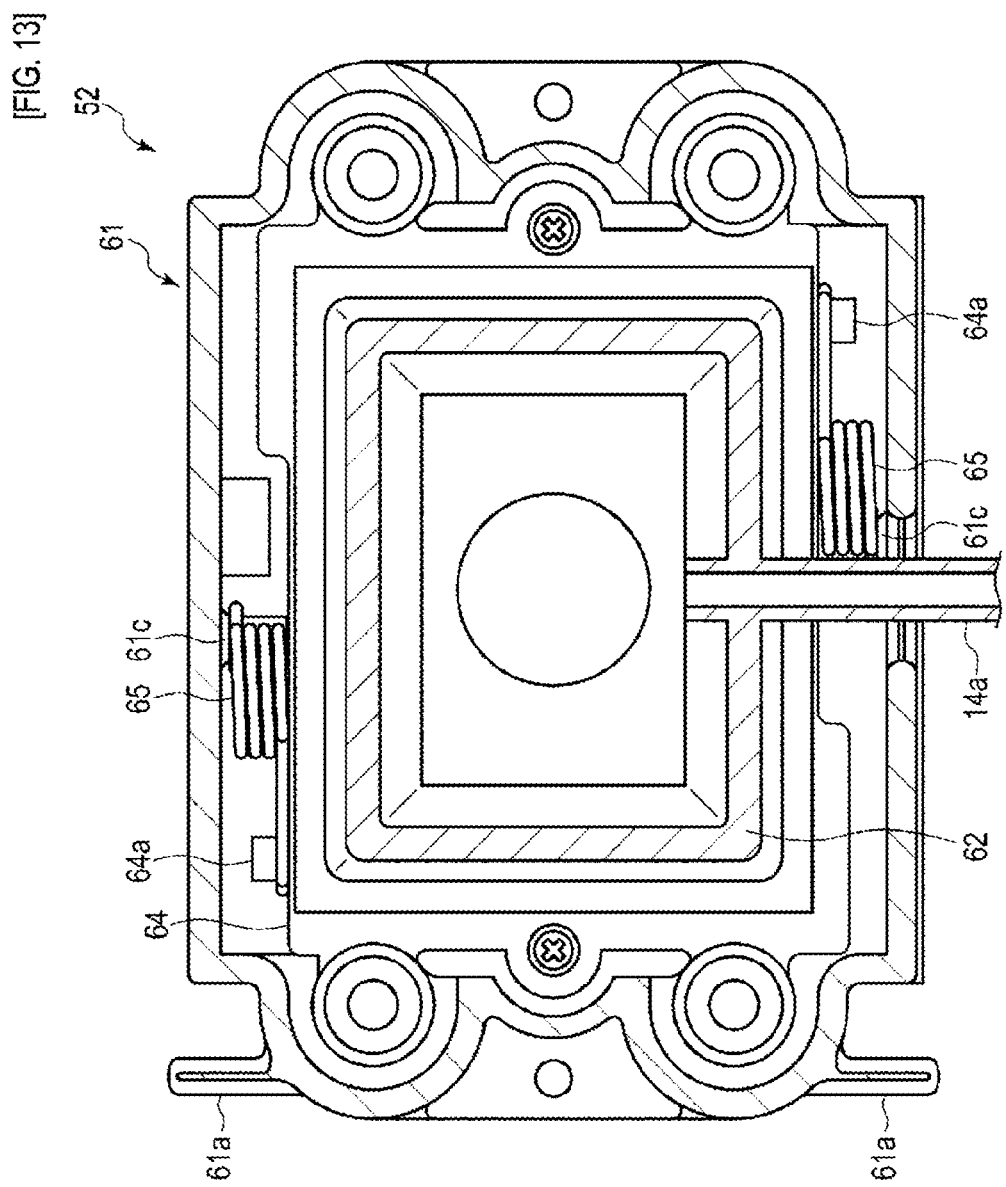

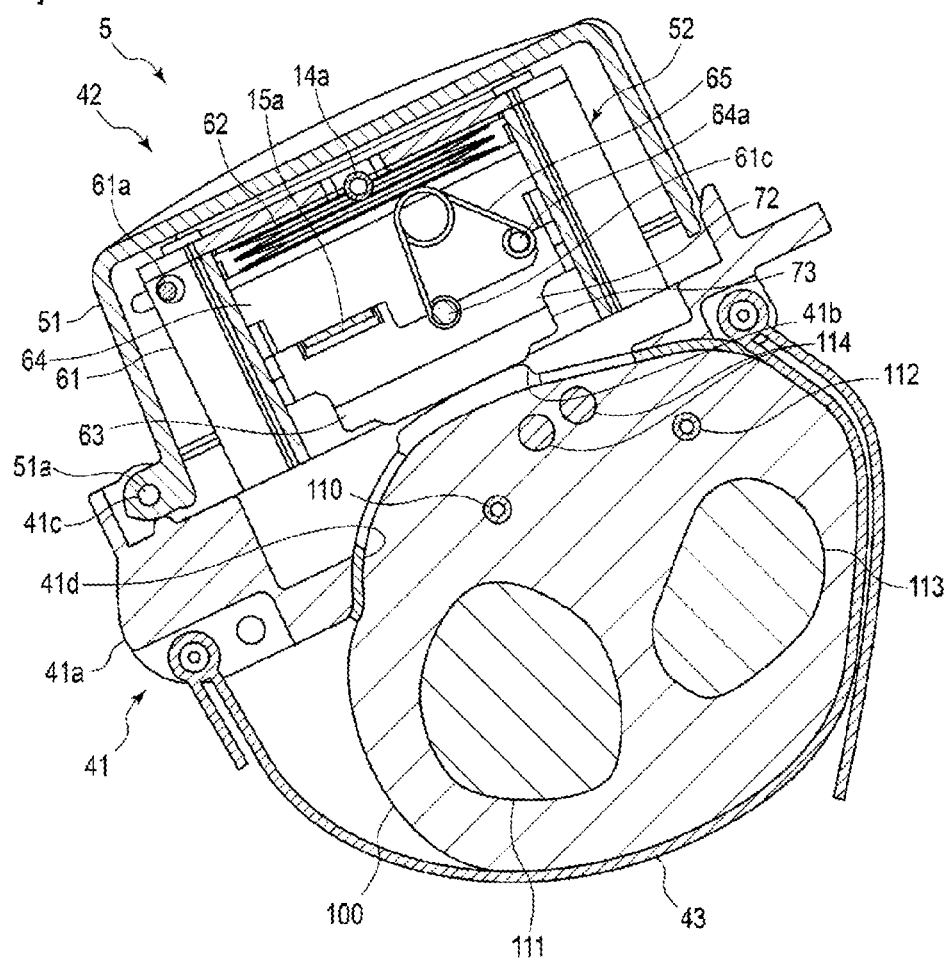
[FIG. 14]

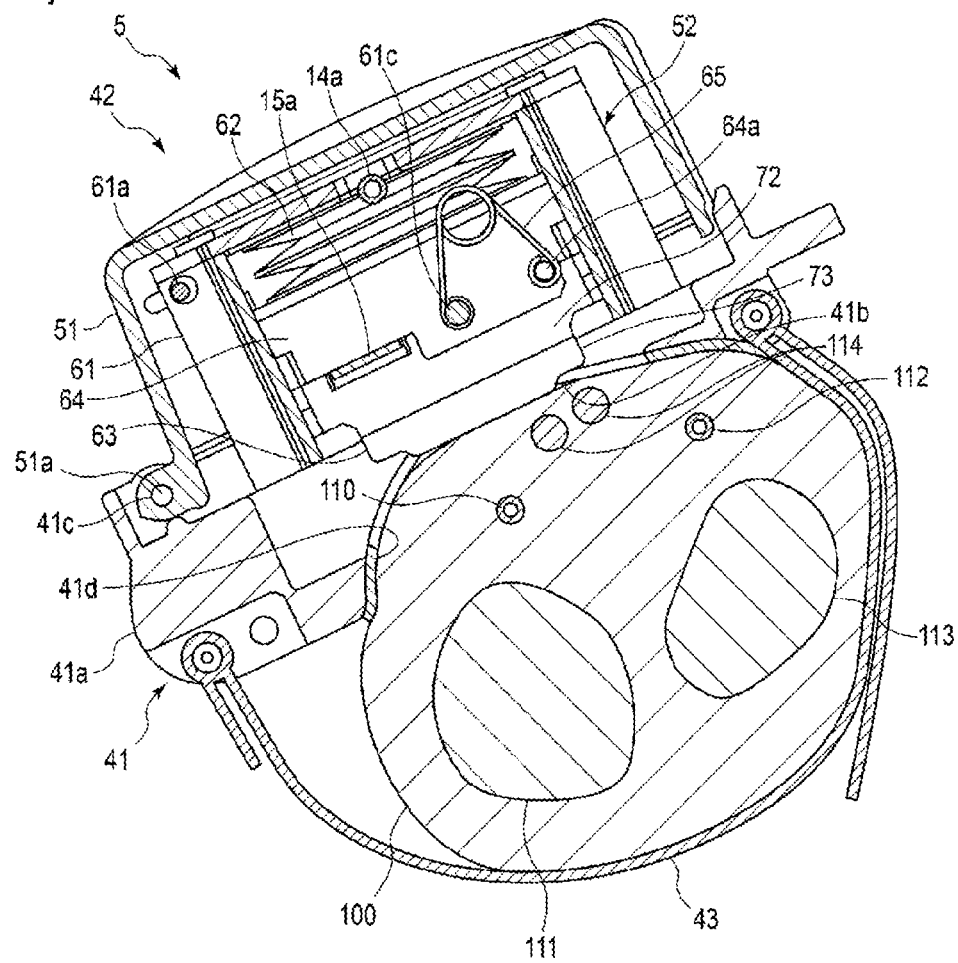
[FIG. 15]

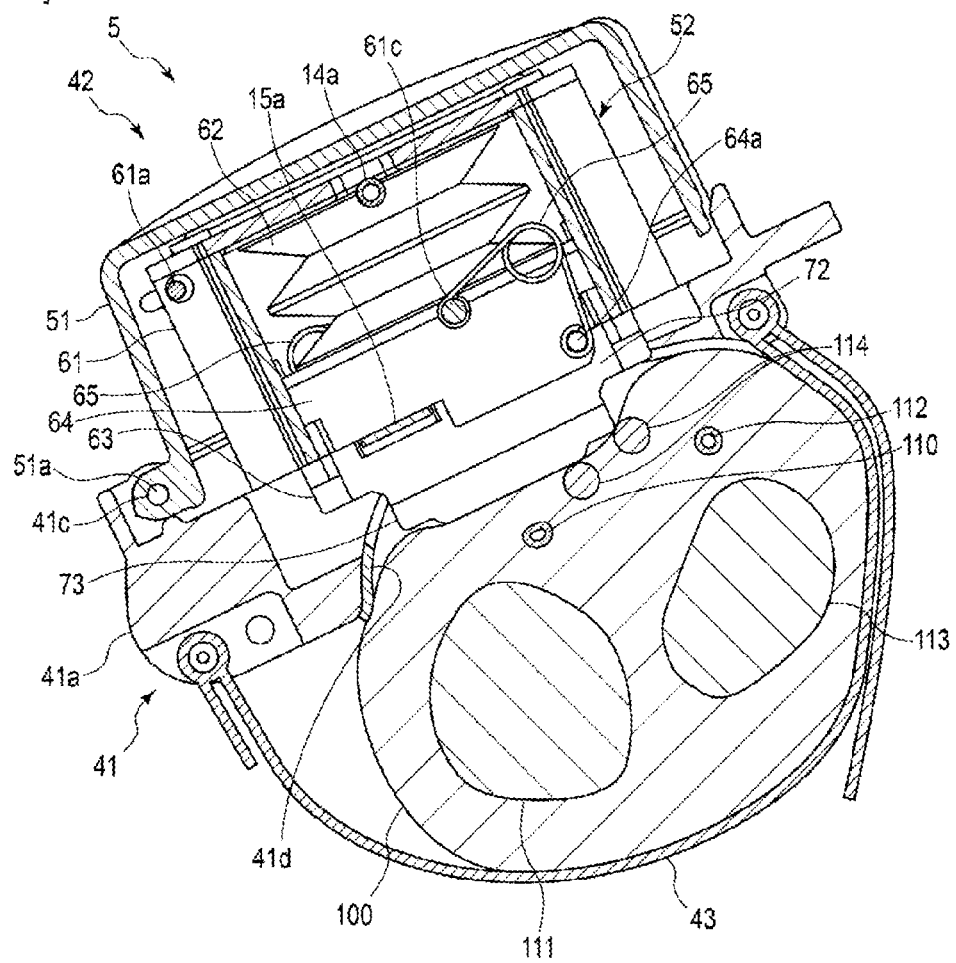
[FIG. 16]

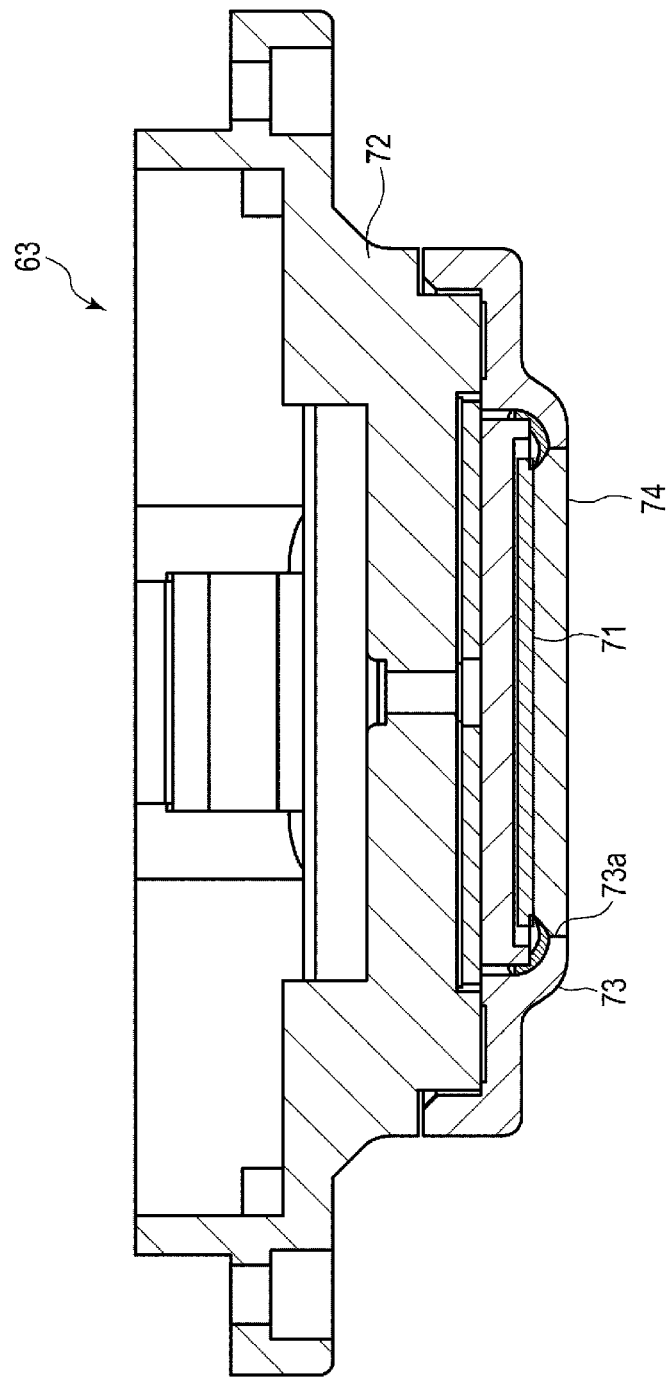
[FIG. 17]

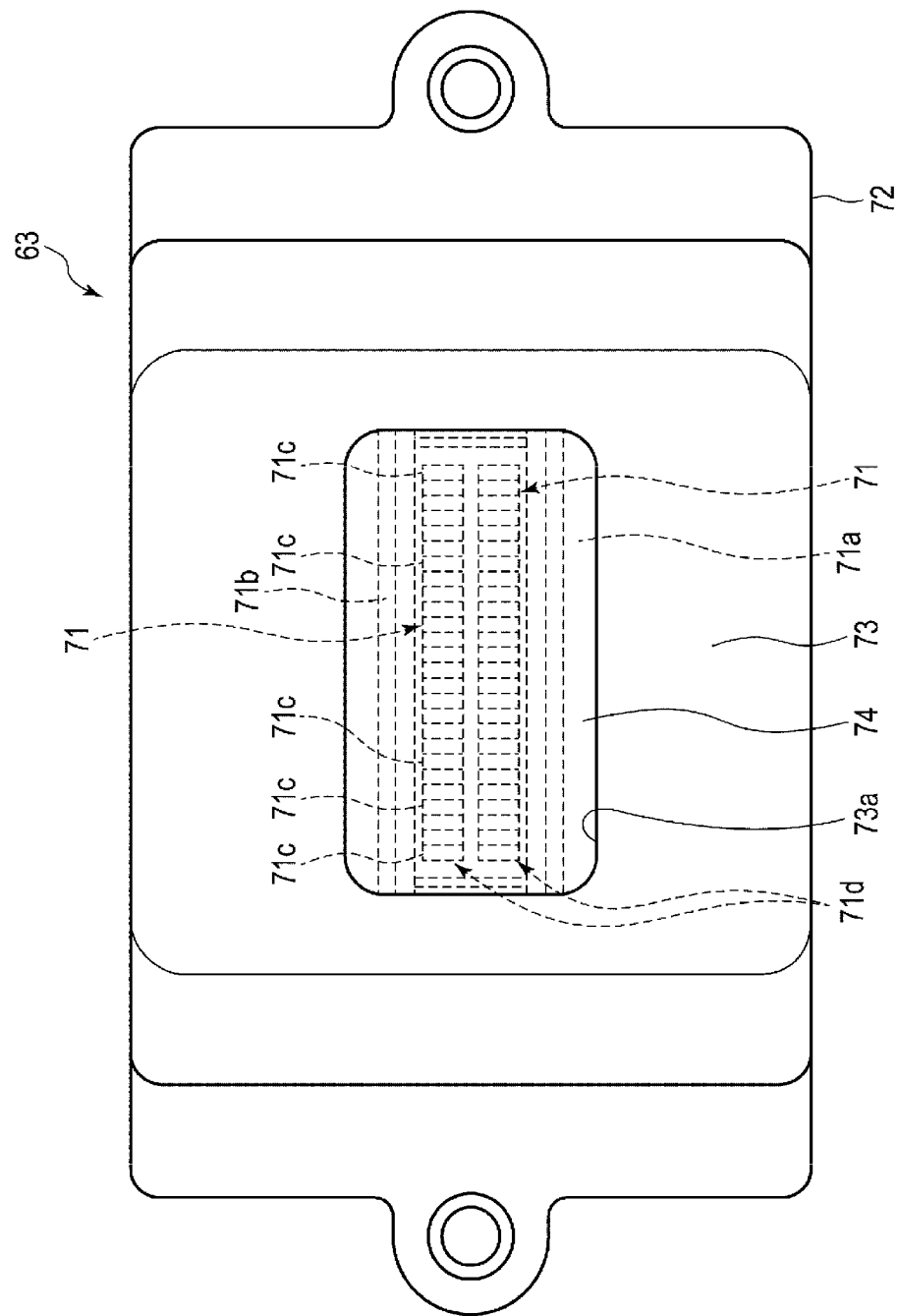
[FIG. 18]

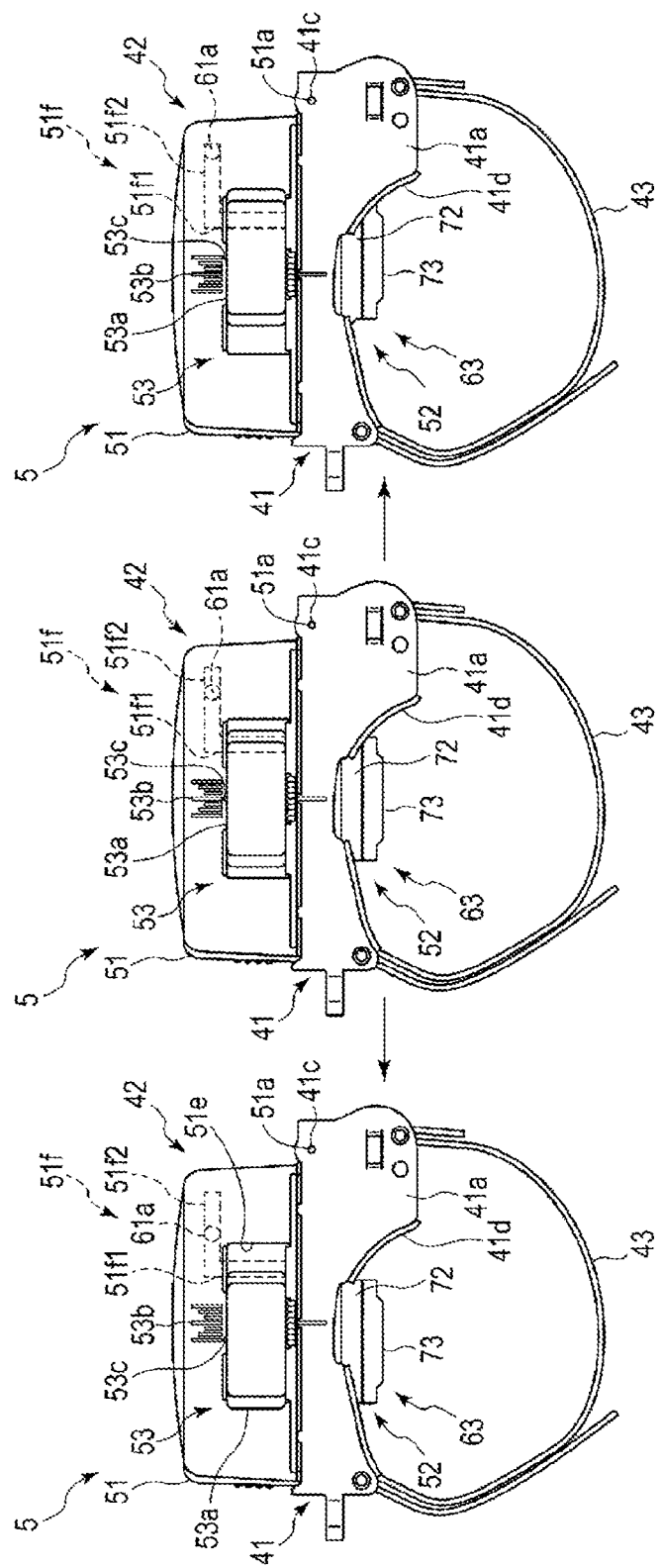
[FIG. 19]

[FIG. 20]
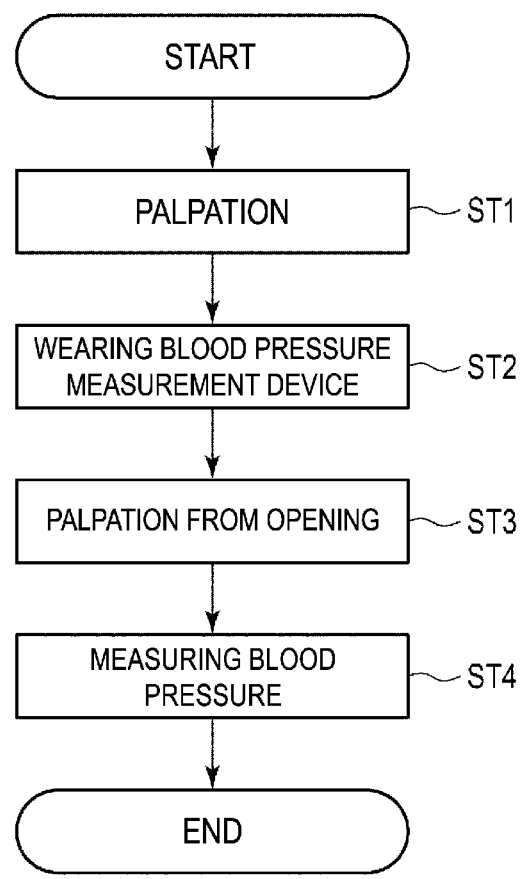

[FIG. 21]
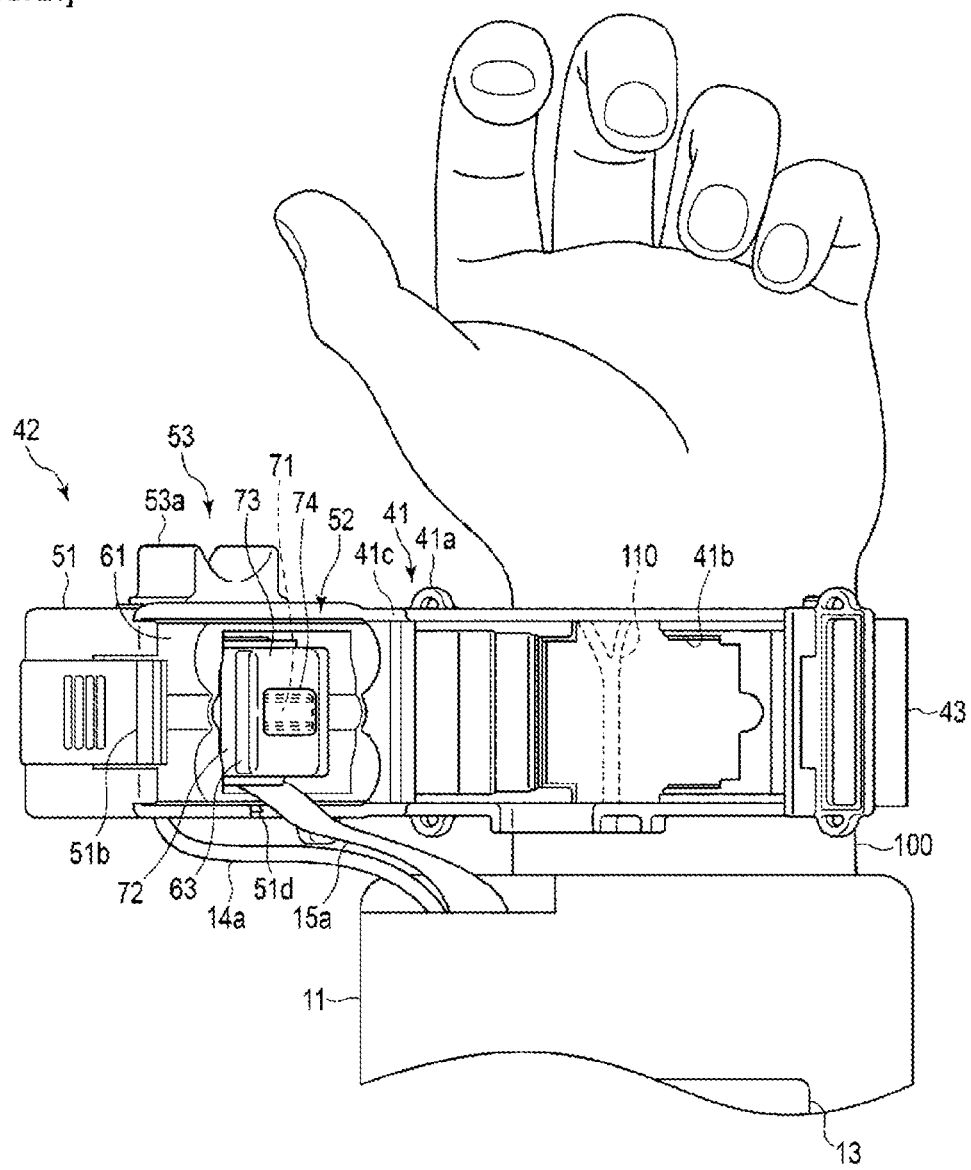

[FIG. 22]
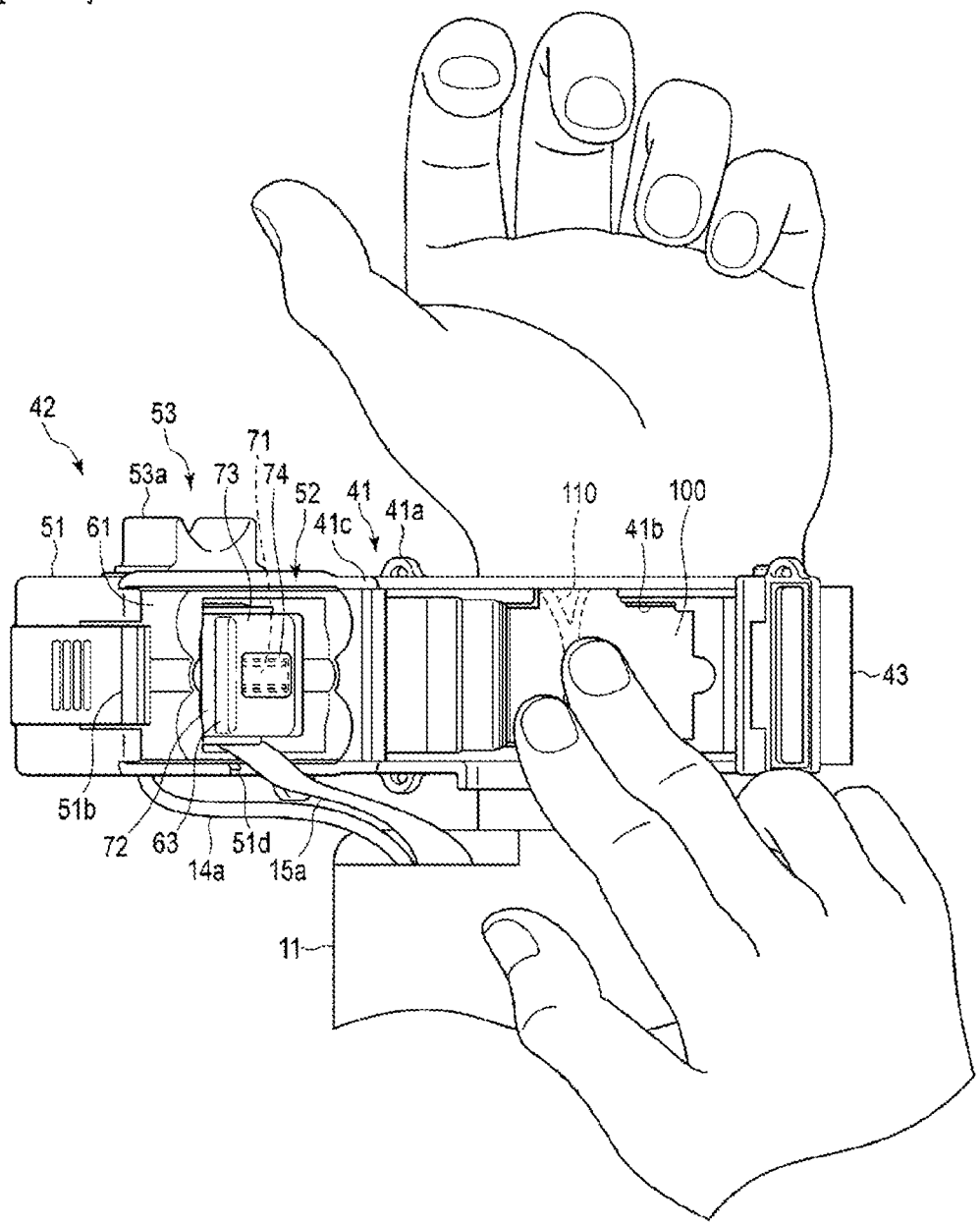

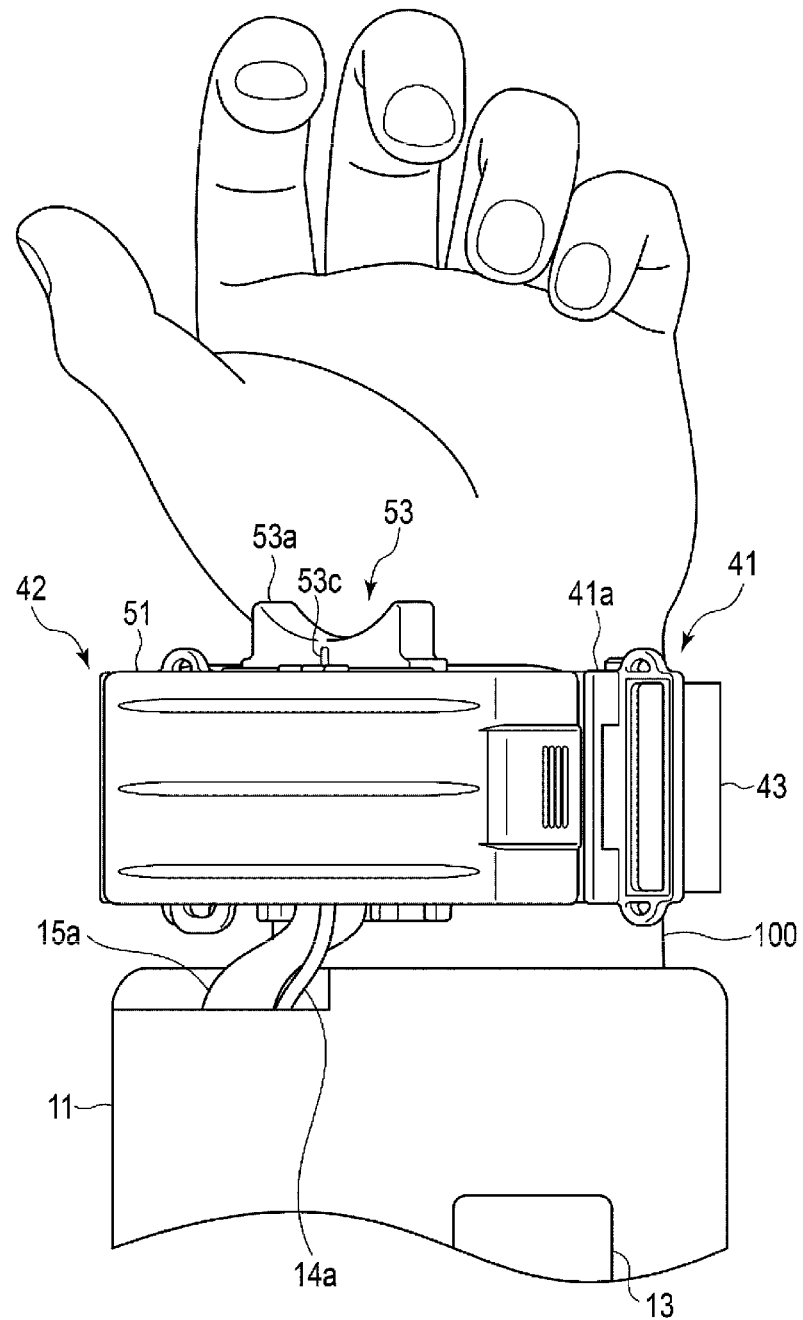
[FIG. 23]

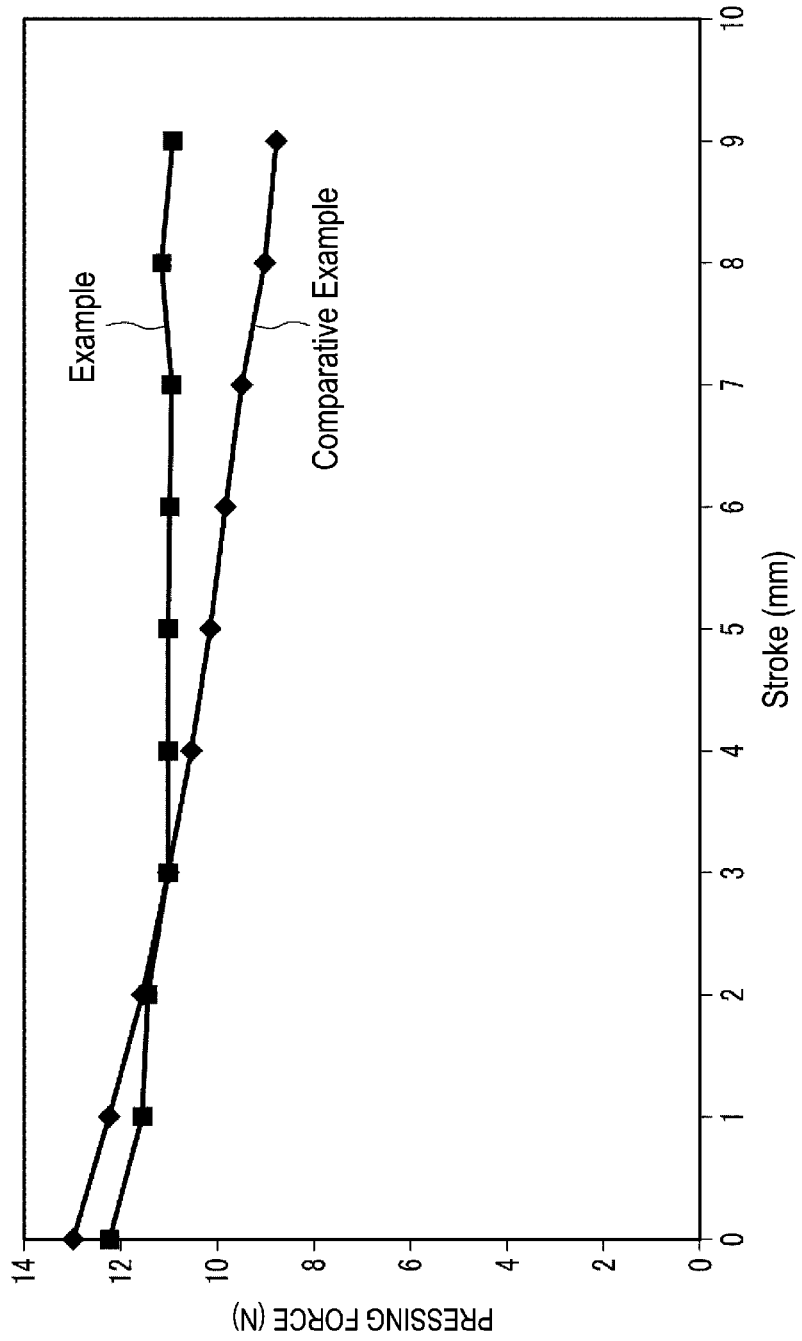
[FIG. 24]

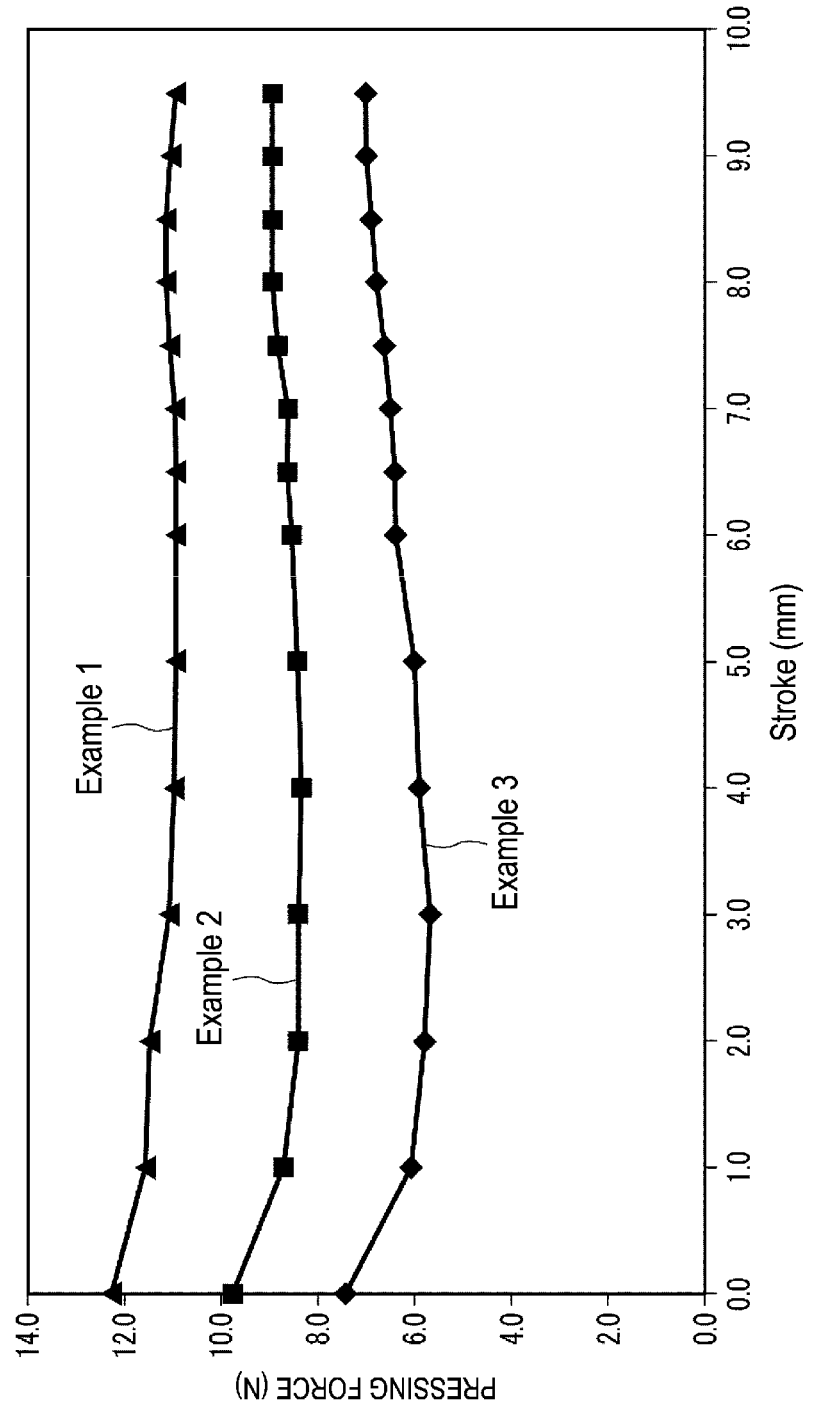
[FIG. 25]

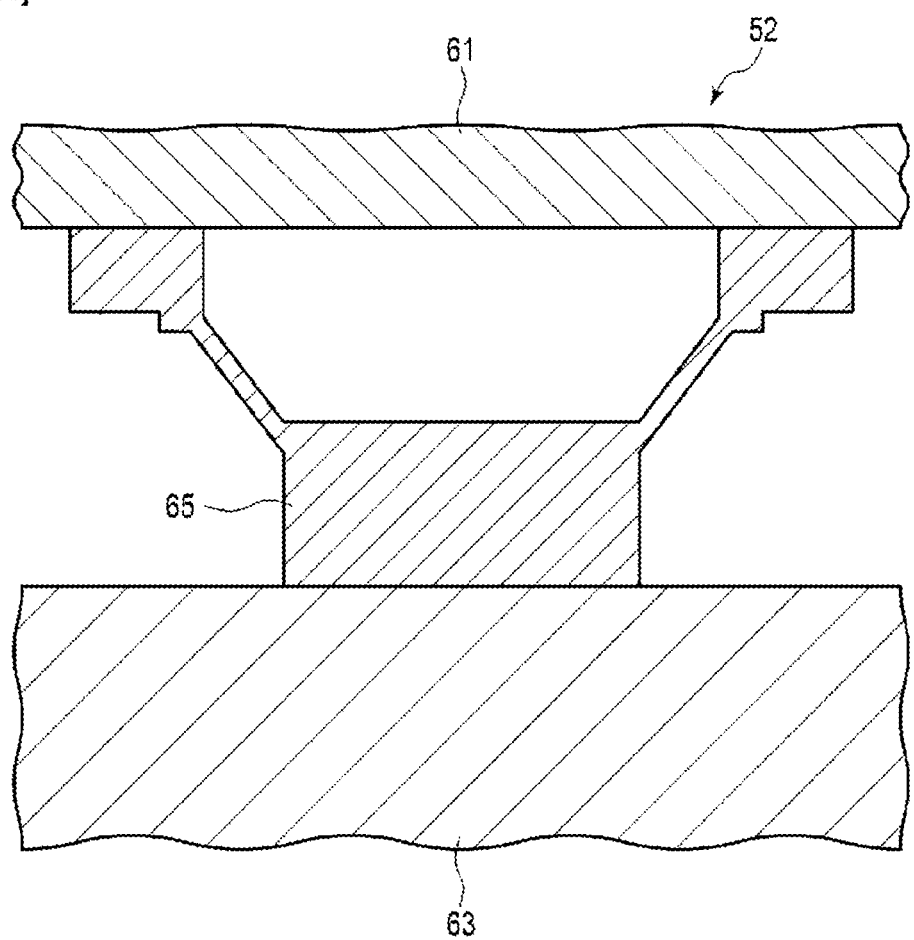
[FIG. 26]

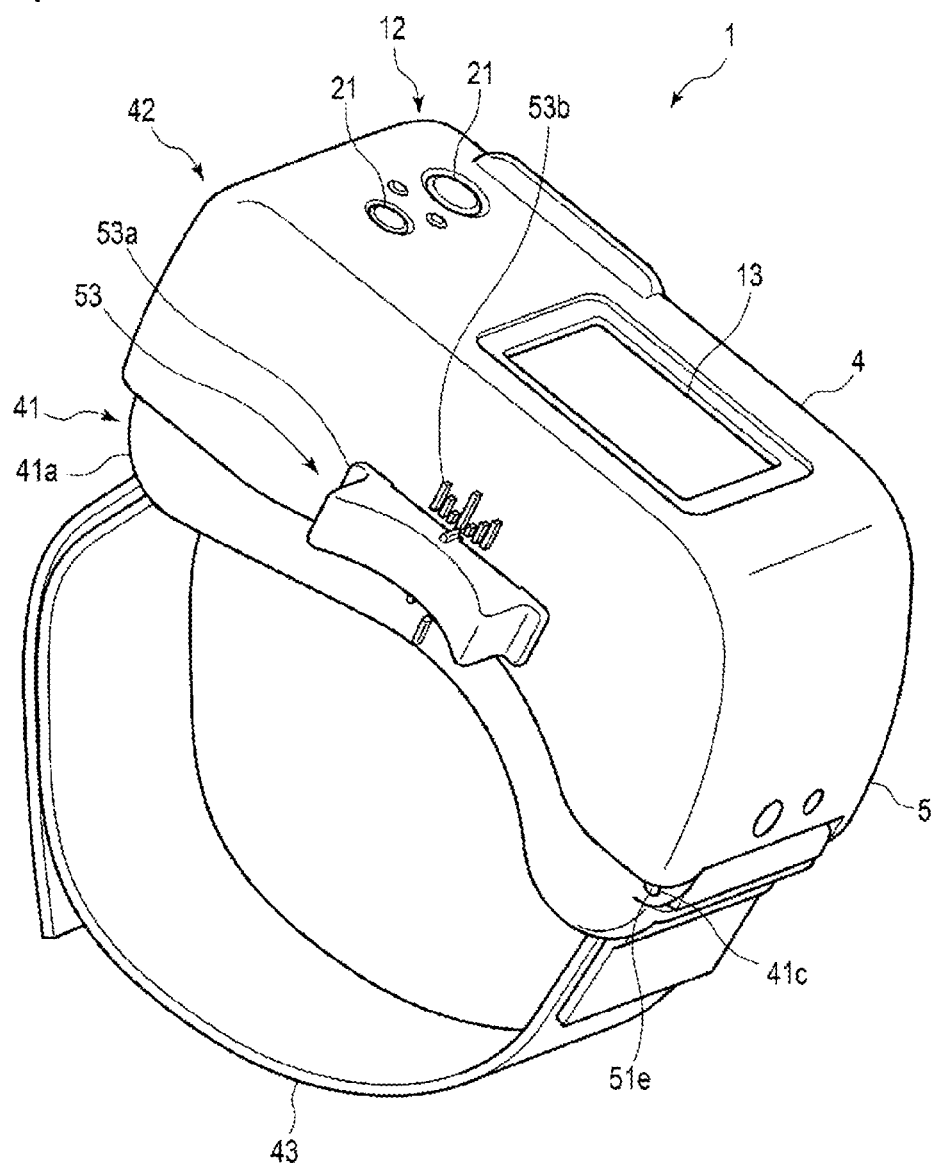
[FIG. 27]

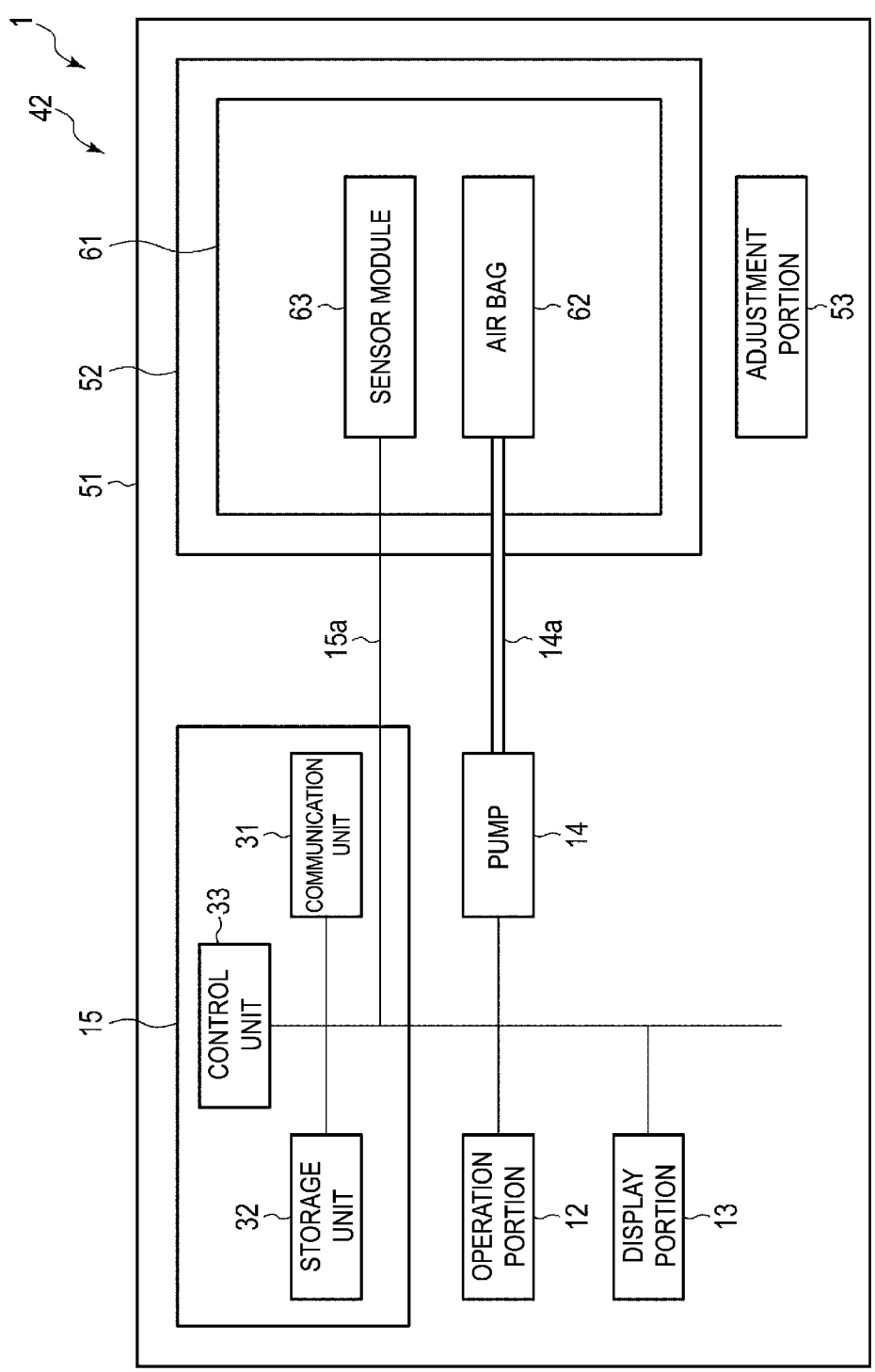

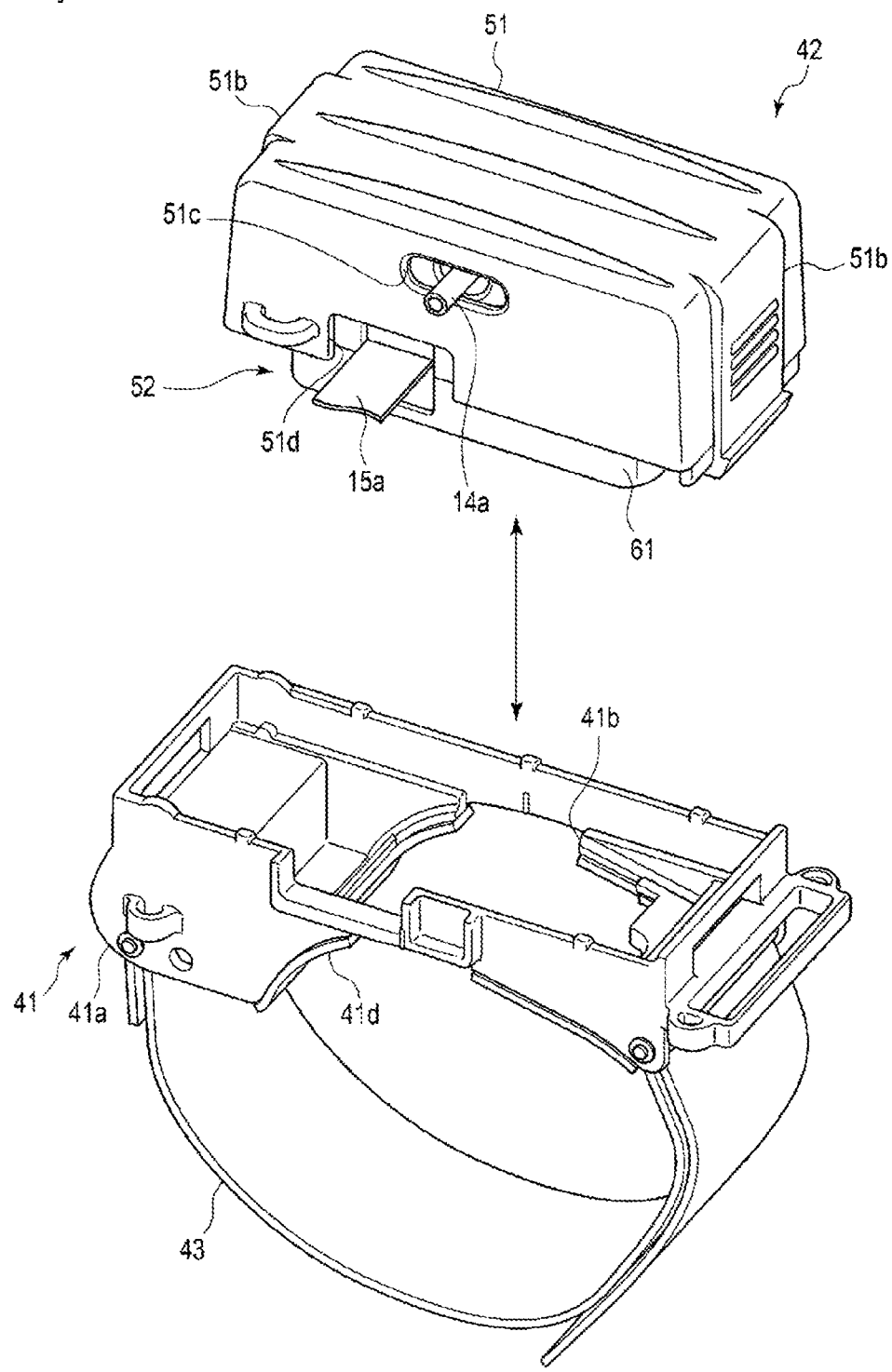
[FIG. 29]

BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/020051, filed May 21, 2019, which application claims priority from Japanese Patent Application No. 2018-099735, filed May 24, 2018, which applications are incorporated herein by reference in their entireties.

TECHNICAL FIELD

The present invention relates to a blood pressure measurement device for measuring blood pressure.

BACKGROUND ART

In recent years, blood pressure measurement devices for measuring blood pressure are being used to monitor health status at home, as well as in medical facilities. In such blood pressure measurement devices, for example, known technologies using the oscillometric method, the tonometry method as described in JP H01-288228 A, and the like are used. A blood pressure measurement device using the oscillometric method detects vibration of the artery wall and measures blood pressure by using pressure sensor to detect the pressure of a cuff wrapped around the upper arm or wrist of a living body.

Also, a blood pressure measurement device using the tonometry method measures blood pressure by bringing a sensor module including a plurality of pressure sensors into contact with a region of the wrist where the artery is found. Such blood pressure measurement devices using the tonometry method measures blood pressure per beat, for example, by pressing a radial artery, one artery of the arm, with a sensor module to form a flat portion in the artery, and measuring the pressure pulse wave with the interior and exterior of the radial artery in a balanced state.

CITATION LIST

Patent Literature

Patent Document 1: JP H01-288228 A

SUMMARY OF INVENTION

Technical Problem

It is conceivable that a blood pressure measurement device using the tonometry method described above, to form a flat portion in the artery, uses a drive mechanism to press the sensor module against the wrist to a position whereby a flat portion is formed in the artery. The drive mechanism brings the sensor module into contact with the wrist from a position spaced apart from the wrist, for example, and further moves the sensor module. For example, as such a drive mechanism, a configuration is conceivable in which the sensor module is moved toward the wrist by expanding an air bag to press against the sensor module. However, as the air bag expands and the stroke amount of the sensor module increases, the pressing force of the air bag pressing against the sensor module problematically decreases. When the pressing force of the air bag pressing against the sensor module decreases, an unfavorable flat portion may be formed in the artery.

Thus, an object of the present invention is to provide a blood pressure measurement device that can suitably press the sensor module against the wrist with a simple configuration.

Solution to Problem

According to an aspect, provided is a blood pressure measurement device, including:
an attach portion including:
 an opening portion provided at a position opposite a region where one artery of a wrist is found and
 an end surface that curves conforming to a shape in a circumferential direction of a portion of the wrist;
a fastener provided on the attach portion; and
a sensing body including:
 a sensor unit disposed opposite the opening portion, the sensor unit including a sensor module that comes into contact with the region where the one artery of the wrist is found and an air bag that presses the sensor module toward the wrist by expanding when the device is worn on the wrist,
 a case that houses the sensor module in a manner allowing the sensor module to move in one direction with respect to the opening portion, and
 a biasing member that biases the sensor module in a direction toward the wrist.

Here, the region in which one artery of the wrist is found is the region in which the radial artery or the ulnar artery of the wrist is found and preferably is the region in which the radial artery is found.

According to this aspect, the biasing member is configured to bias the sensor module toward the wrist. Thus, during blood pressure measurement, the biasing member also presses the sensor module toward the wrist when the sensor module is pressed toward the wrist by the air bag. Thus, the blood pressure measurement device can suitably press the sensor module against the wrist by the biasing member assisting in pressing, even if the amount of stroke of the sensor module increases and the pressing force at which the air bag presses the sensor module is reduced. As a result, the blood pressure measurement device can form a preferred flat portion in the artery.

Provided is a blood pressure measurement device according to the blood pressure measurement device of the aspect described above, wherein the biasing member biases the sensor module in the direction toward the wrist when an end of the sensor module is located on a side of the wrist from a neutral point, the neutral point being a predetermined position with respect to the opening portion, and biases the sensor module in a direction away from the wrist when the end of the sensor module is located at a position further away from the wrist than the neutral point.

According to this aspect, the biasing member biases the sensor module in a direction toward the wrist with force along one direction, with the neutral point of the sensor module acting as the boundary, when the sensor head cover is positioned closer to the wrist than the neutral point. According to this configuration, when the blood pressure measurement device is used for blood pressure measurement, the air bag and the biasing member press the sensor module toward the wrist, allowing the sensor head cover to be suitably pressed against the wrist.

Also, according to this configuration, the biasing member biases the sensor module in a direction away from the wrist when the end of the sensor module is at a position separated from the wrist further than the neutral point. Thus, after blood pressure measurement, the sensor module is biased and moved by the bias member in a direction away from the wrist with force along one direction, and the sensor module is located inside the case more so than the opening portion. Thus, when removing the worn blood pressure measurement device, the sensor module does not project outward.

Provided is a blood pressure measurement device according to the blood pressure measurement device of the aspect described above, wherein the neutral point is a position where the end of the sensor module projects from the opening portion.

According to this aspect, the neutral point is at a position where the end of the sensor module projects from the opening portion, and thus the sensor module can be moved to a position further away from the wrist than the neutral point using the reaction force from the wrist. Thus, the biasing direction of the biasing member can be switched from the direction of pressing the sensor module toward the wrist to a direction of biasing the sensor module away from the wrist.

Provided is a blood pressure measurement device according to the blood pressure measurement device of the aspect described above, wherein the biasing member is a torsion spring.

According to this aspect, the sensor module is biased with the bias member with a simple configuration including a torsion spring. Thus, an increase in manufacturing cost can be prevented.

Provided is a blood pressure measurement device according to the blood pressure measurement device of the aspect described above, wherein a plurality of the torsion springs are provided.

According to this aspect, because a plurality of the torsion springs are provided, the size of the each of the plurality of torsion springs needed to create a desired biasing force can be made small and used as such, compared to a configuration in which a single torsion spring is provided. Thus, the sensor device can keep the space and configuration small for installing and supporting the torsion springs.

Provided is a blood pressure measurement device according to the blood pressure measurement device of the aspect described above, wherein two of the torsion springs are provided on either side of the sensor module in a direction orthogonal to the circumferential direction of the wrist when the device is worn on the wrist, and one end of each of the torsion springs is fixed to the sensor module and the other end of each of the torsion springs is fixed to the case.

According to this aspect, the sensor device includes a pair of the torsion springs disposed with point symmetry on either side of the sensor module. Thus, the torsion springs can uniformly apply a biasing force to the sensor module. This allows the sensor device to apply the biasing force of the torsion springs to the sensor module along the movement direction of the sensor module.

Provided is a blood pressure measurement device according to the blood pressure measurement device of the aspect described above, wherein the biasing member is formed from a resin material and deforms due to an external force in one direction and restores its shape in a direction opposite to the direction in which the external force is applied.

According to this aspect, the biasing member can be formed from a resin material, making design and manufacture easy.

Advantageous Effects of Invention

The present invention provides a blood pressure measurement device that can move the sensor module back and forth in one direction with a simple configuration.

BRIEF DESCRIPTION OF DRAWINGS

FIG. 1 is a perspective view illustrating the configuration of a blood pressure measurement device according to an embodiment of the present invention.

FIG. 2 is a block diagram illustrating the configuration of the blood pressure measurement device.

FIG. 3 is a perspective view illustrating the configuration of a sensor device of the blood pressure measurement device.

FIG. 4 is a perspective view illustrating the configuration of a portion of the sensor device of the blood pressure measurement device.

FIG. 5 is a perspective view illustrating the configuration of a sensor unit of the blood pressure measurement device.

FIG. 6 is a perspective view illustrating the configuration of the sensor unit with a side wall omitted.

FIG. 7 is a perspective view illustrating the configuration of the sensor unit with a side wall omitted.

FIG. 8 is a plan view illustrating the configuration of the sensor unit.

FIG. 9 is a cross-sectional view illustrating the configuration of the sensor module and an air bag of the sensor unit.

FIG. 10 is a cross-sectional view illustrating the configuration of the sensor module and the air bag.

FIG. 11 is a cross-sectional view illustrating the configuration of the sensor module and the air bag.

FIG. 12 is an explanatory diagram illustrating the operation of the sensor unit.

FIG. 13 is a cross-sectional view illustrating the configuration of the sensor module and the air bag.

FIG. 14 is a cross-sectional view illustrating the configuration of the blood pressure measurement device in a state of being attached to the wrist.

FIG. 15 is a cross-sectional view illustrating the configuration of the blood pressure measurement device in a state of being attached to the wrist.

FIG. 16 is a cross-sectional view illustrating the configuration of the blood pressure measurement device in a state of being attached to the wrist.

FIG. 17 is a cross-sectional view illustrating the configuration of the sensor module of the sensor unit.

FIG. 18 is a plan view illustrating the configuration of the sensor module.

FIG. 19 is an explanatory diagram illustrating an example of the position adjustment of the sensor unit of the blood pressure measurement device.

FIG. 20 is a flowchart illustrating an example of blood pressure measurement using the blood pressure measurement device.

FIG. 21 is an explanatory diagram illustrating an example of blood pressure measurement using the blood pressure measurement device.

FIG. 22 is an explanatory diagram illustrating an example of blood pressure measurement using the blood pressure measurement device.

FIG. 23 is an explanatory diagram illustrating an example of blood pressure measurement using the blood pressure measurement device.

FIG. 24 is an explanatory diagram illustrating the relationship between stroke and pressing force of the blood pressure measurement device.

FIG. 25 is an explanatory diagram illustrating the relationship between stroke and pressing force of the blood pressure measurement device.

FIG. 26 is a cross-sectional view illustrating the configuration of a biasing member of a sensor unit according to another embodiment of the present invention.

FIG. 27 is a perspective view illustrating the configuration of a blood pressure measurement device according to another embodiment of the present invention.

FIG. 28 is a block diagram illustrating the configuration of the blood pressure measurement device.

FIG. 29 is a perspective view illustrating the configuration of a blood pressure measurement device according to another embodiment of the present invention.

DESCRIPTION OF EMBODIMENTS

First Embodiment

An example of a blood pressure measurement device 1 according to the first embodiment of the present invention is described below using FIGS. 1 to 18.

FIG. 1 is a perspective view illustrating the configuration of the blood pressure measurement device 1 according to an embodiment of the present invention in a state in which a body fastener 16 is closed. FIG. 2 is a block diagram illustrating the configuration of the blood pressure measurement device 1. FIG. 3 is a perspective view illustrating the configuration of a sensor device 5 of the blood pressure measurement device 1 in a state in which a sensing body 42 is open. FIG. 4 is a perspective view illustrating the configuration of the blood pressure measurement device 1 with a sensor unit 52 removed from the sensor device 5. FIG. 5 is a perspective view illustrating the configuration of the sensor unit 52 of the blood pressure measurement device 1. FIG. 6 is a perspective view illustrating the configuration of the sensor unit 52 with a side wall omitted. FIG. 7 is a perspective view illustrating the configuration of the sensor unit 52 with a side wall omitted. FIG. 8 is a plan view illustrating the configuration of the sensor unit 52.

FIG. 9 is a cross-sectional view illustrating the configuration of a sensor module 63 and an air bag 62 of the sensor unit 52 taken along a cross-section line IX-IX in FIG. 8. FIG. 10 is a cross-sectional view illustrating the configuration of the sensor module 63 and the air bag 62 taken along a cross-section line X-X in FIG. 8. FIG. 11 is a cross-sectional view illustrating the configuration of the sensor module 63 and the air bag 62 taken along a cross-section line XI-XI in FIG. 8. FIG. 12 is an explanatory diagram illustrating the operation of the sensor unit 52. FIG. 13 is a cross-sectional view illustrating the configuration of the sensor module 63 and the air bag 62 of the sensor unit 52 taken along a cross-section line XIII-XIII in FIG. 9. FIGS. 14 to 16 are cross-sectional views illustrating the configuration of the blood pressure measurement device 1 in a state of being attached to a wrist 100. FIG. 17 is a cross-sectional view illustrating the configuration of the sensor module 63 of the sensor unit 52. FIG. 18 is a plan view illustrating the configuration of the sensor module 63 of the sensor unit 52.

Note that in the drawings, a radial artery of a wrist 100 is denoted as 110, a radius is denoted as 111, an ulnar artery is denoted as 112, an ulna is denoted as 113, and a tendon is denoted as 114.

The blood pressure measurement device 1 is an electronic blood pressure measurement device that is attached to the wrist 100 of a living body and calculates a blood pressure value from the pressure of the radial artery 110. As illustrated in FIGS. 1 to 18, the blood pressure measurement device 1 includes a device body 4 and the sensor device 5. For example, the blood pressure measurement device 1 has a configuration in which the sensor device 5 is attached to a region of the wrist 100 where the radial artery 110 is found and in which the device body 4 is attached to the wrist 100 adjacent to the sensor device 5 on the elbow side.

The blood pressure measurement device 1, by pressing the radial artery 110 with the sensor device 5, measures the pressure of the pressure pulse wave per heart beat that changes in conjunction with the heart rate of the radial artery 110. In addition, the blood pressure measurement device 1 executes, via the device body 4, processing based on the tonometry method on the measured pressure and obtains the blood pressure.

As illustrated in FIGS. 1 and 2, the device body 4 includes: a body case 11, an operation portion 12, a display portion 13, a pump 14, a control board 15, and the body fastener 16. Also, for example, the device body 4 may be provided with a cuff on the body fastener 16 that is configured to compress the wrist 100 during blood pressure measurement.

The body case 11 houses: a portion of the operation portion 12, a portion of the display portion 13, and the control board 15 and exposes: a portion of the operation portion 12 and a portion of the display portion 13 from the outer surface. In addition, the body fastener 16 is attached to the body case 11.

The operation portion 12 is configured to receive an instruction input from a user. For example, the operation portion 12 includes: a plurality of buttons 21 provided on the body case 11 and a sensor that detects operation of the buttons 21. Note that the operation portion 12 may be provided on the display portion 13 as a touch panel. When operated by the user, the operation portion 12 converts an instruction into an electrical signal. The sensor that detects operation of the buttons 21 is electrically connected to the control board 15 and outputs an electrical signal to the control board 15.

The display portion 13 is disposed in the body case 11 and is exposed from the outer surface of the body case 11. The display portion 13 is electrically connected to the control board 15. The display portion 13 is, for example, a liquid crystal display or an organic electroluminescent display. The display portion 13 displays various information including measurement results such as date and time; blood pressure values like maximum blood pressure and minimum blood pressure; heart rate; and the like.

The pump 14 is, for example, a piezoelectric pump. The pump 14 includes a tube 14a connected to the sensor device 5 for compressing air and supplying compressed air to the sensor device 5 via the tube 14a. The pump 14 is electrically connected to the control board 15.

As illustrated in FIG. 2, the control board 15 includes a communication unit 31, a storage unit 32, and a control unit 33, for example. The control board 15 is configured by the communication unit 31, the storage unit 32, and the control unit 33 being mounted on the board. Also, the control board 15 is connected to the sensor device 5 via a cable 15a. The cable 15a runs from inside the body case 11 to outside the body case 11 via a portion of the outer surface of the body case 11. For example, the cable 15a runs from inside the body case 11 to the sensor device 5 via an opening formed in a side surface of the body case 11.

The communication unit 31 is configured to transmit and receive information from an external device wirelessly or via a wire. The communication unit 31 transmits information, such as information controlled by the control unit 33, measured blood pressure values, pulse, and the like, to an external device via a network and receives a program for software update or the like from an external device via a network and sends this to the control unit.

In the present embodiment, the network is, for example, the Internet, but no such limitation is intended. The network may be a network such as a Local Area Network (LAN) provided in a hospital or may be a direct wired communication with an external device, using a cable or the like including terminals of a predetermined protocol such as USB. Thus, the communication unit 31 may include a plurality of wireless antennas, micro-USB connectors, or the like.

The storage unit 32 pre-stores: program data for controlling the entire blood pressure measurement device 1; settings data for configuring various functions of the blood pressure measurement device 1; calculation data for calculating blood pressure values and pulse from the pressure measured by pressure sensitive elements 71c; and the like. Furthermore, the storage unit 32 stores information such as: the calculated blood pressure value; pulse; time series data in which this calculated data and time are associated; and the like.

The control unit 33 is composed of, for example, a single or a plurality of central processing units (CPU). The control unit 33 controls the operation of the entire blood pressure measurement device 1 and executes each processing on the basis of the program data. The control unit 33 is electrically connected to the operation portion 12, the display portion 13, the pump 14, and the sensor device 5, controls the operation of each configuration, transmits and receive signals, and supplies power.

The body fastener 16 includes, for example, one or a plurality of band-like bands; and a fixing member such as a hook-and-loop fastener that secures the band wrapped around the wrist 100. The body fastener 16 fixes the body case 11 to the wrist 100.

With the device body 4 having such a configuration, by the control unit 33 executing processing using the program data stored in the storage unit 32, blood pressure data can be continuously generated from the pulse waves of the radial artery 110 detected by the sensor device 5. The blood pressure data includes data of blood pressure waveforms corresponding to the waveforms of measured pulse waves. The blood pressure data may further include time series data of a blood pressure feature value (blood pressure value). The blood pressure feature value includes, for example and without limitation, systolic blood pressure (SBP) and diastolic blood pressure (DBP). The maximum value in the pulse wave waveform per heart beat corresponds to systolic blood pressure, and the minimum value in the pulse wave waveform of per heart beat corresponds to diastolic blood pressure.

In this embodiment, the device body 4 measures the pressure pulse wave as a pulse wave by the tonometry method. Here, the tonometry method refers to a method for pressing the radial artery 110 from above the skin with appropriate pressure, forming a flat portion in the artery, and measuring the pressure pulse wave with the sensor device 5 in a balanced state between the interior and the exterior of the radial artery 110. According to the tonometry method, a blood pressure value per heart beat can be acquired.

As illustrated in FIGS. 1, 3, and 4, the sensor device 5 includes: an attach portion 41, the sensing body 42, and a fastener 43.

The attach portion 41 includes a main surface that has a shape that conforms to the circumferential direction of the wrist 100 in the region where the radial artery 110 of the left wrist 100 is found. As a specific example, the attach portion 41 includes: a base portion 41a that curves conforming to the shape in the circumferential direction of the wrist 100 in the region in contact with the wrist 100; an opening portion 41b formed in the base portion 41a; an attachment portion 41c provided on the base portion 41a for attaching the sensing body 42; and a cushion 41d provided on a main surface of the base portion 41a that comes into contact with the wrist 100.

The base portion 41a is configured to be elongated in one direction. The base portion 41a is disposed on a palm side of wrist 100 and on a side portion side on the radius 111 side of the wrist 100, and the main surface disposed on the wrist 100 side curves conforming to the shape in the circumferential direction of the palm side of the wrist 100 and the side portion side on the radius 111 side of the wrist 100. Furthermore, at least the outer circumferential edge side of the main surface of the base portion 41a comes into contact with the sensing body 42.

The opening portion 41b is provided in a central region of the base portion 41a and is formed with a size of one or a plurality of fingers. That is, the opening portion 41b is formed with a size that allows the region where the radial artery 110 of the wrist 100 is exposed from the opening portion 41b to be palpated by a finger, when the sensor device 5 is attached to the wrist 100, and that allows a portion of the sensing body 42 to come into contact with the wrist 100.

The attachment portion 41c is provided on a main surface of the base portion 41a opposite the surface facing the wrist 100 and provided on an end side of the base portion 41a in the longitudinal direction. The attachment portion 41c supports the sensing body 42 and is configured to move the sensing body 42 in a direction away from the base portion 41a and a direction toward the base portion 41a. As a specific example, the attachment portion 41c is a journal-like portion that rotatably journals the sensing body 42 about an axis. For example, the attachment portion 41c is integrally formed with the base portion 41a.

The cushion 41d is, for example, an elastic body configured in a sheet shape from a foaming resin material provided on a main surface of the base portion 41a that comes into contact with the wrist 100. The cushion 41d protects wrist 100 by elastically deforming, for example, when the blood pressure measurement device 1 is worn on the wrist 100.

As illustrated in FIGS. 2 to 16, the sensing body 42 includes: a case 51, the sensor unit 52, and an adjustment portion 53 for adjusting the position of the sensor unit 52.

The case 51 has a rectangular box shape with an open surface opposite the attach portion 41, for example. The case 51 supports the sensor unit 52 and the adjustment portion 53. Furthermore, the case 51 is attached to the attachment portion 41c in a manner to be movable back and forth in a direction away from the base portion 41a. As a specific example, the case 51 includes a rotation shaft 51a rotatably disposed in the attachment portion 41c. Also, the case 51 includes an engagement portion 51b that fixes the case 51 to the base portion 41a when it comes into contact with the base portion 41a. The engagement portion 51b, for example, is a projection that engages with an opening provided on the base portion 41a and, by being operated, is configured to release the engagement with the opening of the base portion 41a.

Furthermore, the case 51 includes: a first hole portion 51c where the tube 14a is disposed, a second hole portion 51d where the cable 15a is disposed, a third hole portion 51e that movably supports a portion of the adjustment portion 53, and a guide groove 51f that guides the movement of the sensor unit 52.

The first hole portion 51c and the second hole portion 51d are provided on the same side wall of the case 51 adjacent to the device body 4 when the device is worn on the wrist 100.

The third hole portion 51e is provided on a side wall opposite to the side wall of the case 51 where the first hole portion 51c and the second hole portion 51d are provided. The third hole portion 51e is a rectangular opening that linearly extends in the longitudinal direction of the case 51, or in other words, the circumferential direction of the wrist 100 when the sensor device 5 is attached to the wrist 100.

The guide groove 51f is provided on the inner surface side of the side wall of the case 51 provided with the third hole portion 51e. The guide groove 51f includes: a first groove 51f1 that extends from an opening end portion of the case 51 to partway toward the ceiling opposite the opening; and a second groove 51f2 that extends in a direction orthogonal to the first groove 51f1. The second groove 51f2 connects to the first groove 51f1 at one end and extends from this end to the other end toward one side in the longitudinal direction of the case 51.

The sensor unit 52 includes: a movable case 61, the air bag 62, the sensor module 63, a movable base 64 that supports the sensor module 63 to be movable in one direction with respect to the movable case 61, and a biasing member 65 that biases the sensor module 63 with respect to the movable case 61 in one direction. The sensor unit 52 is supported by the case 51 in a manner to be movable in a predetermined range in the longitudinal direction of the case 51 via the adjustment portion 53.

The movable case 61 houses the sensor module 63 and the movable base 64 and supports the movable base 64 supporting the sensor module 63 in a manner allowing the movable base 64 to move toward the opening portion 41b of the attach portion 41. The movable case 61 is supported in a manner to be movable in the longitudinal direction of the case 51 inside the case 51. In addition, a portion of the biasing member 65 is fixed to the movable case 61.

As a specific example, the movable case 61 has a rectangular box shape with the surface opposite the attach portion 41 housing the air bag 62 and the sensor module 63 being open. The movable case 61 houses the air bag 62, the sensor module 63, and the movable base 64. In the movable case 61, the air bag 62 is disposed between the ceiling and the movable base 64. The movable case 61 supports the movable base 64 in a manner allowing the movable base 64 to move in one direction so that the sensor module 63 can protrude out from the opening of the movable case 61.

The movable case 61 includes: a guide projection 61a disposed on the outer surface of the side wall opposite the side wall on which the guide groove 51f of the case 51 is provided in a manner allowing the guide projection 61a to move in the guide groove 51f; a fixing portion 61b in which a portion of the adjustment portion 53 is fixed; and a first support portion 61c that supports a portion of the biasing member 65. As the guide projection 61a moves in the second groove 51f2, the movable case 61 moves in the longitudinal direction of the case 51.

The first support portion 61c supports a portion of the biasing member 65. For example, the first support portion 61c is, for example, a cylindrical projection. The number of first support portions 61c provided is the same as the number of biasing members 65 provided. As a specific example, two first support portion 61c are provided. The two first support portions 61c are provided on the inner surface of opposite side walls of the movable case 61 in a direction orthogonal to the circumferential direction of the wrist 100 when the sensor device 5 is worn on the wrist 100. The first support portions 61c are disposed at a position separated by a certain distance L from the opening end of the movable case 61 disposed on the wrist 100 side. Thus, as illustrated in FIG. 12, a portion of the biasing member 65 is supported at a position separated the distance L from the opening end of the movable case 61. In other words, as illustrated in FIG. 12, the biasing member 65 is supported by the first support portion 61c in a manner allowing the biasing member 65 to rotate about the first support portion 61c.

The air bag 62 has a bellows-like structure. The air bag 62 is fluidly connected to the pump 14 via the tube 14a. As illustrated in FIGS. 9 to 16, the air bag 62 expands in a direction from the ceiling of the movable case 61 toward the opening. When the air bag 62 expands, the sensor module 63 is moved from a position where the sensor module 63 is housed within the movable case 61 to a position where the sensor module 63 projects from the opening of the movable case 61 and comes into contact with the wrist 100 via the opening portion 41b of the attach portion 41. The air bag 62 is formed from polyurethane, for example. The air bag 62 together with the pump 14 and the biasing member 65 constitute a pressing mechanism that presses the sensor module 63 toward the wrist 100.

As illustrated in FIGS. 17 and 18, the sensor module 63 includes: the pressure sensor portion 71, the sensor base 72 that supports the pressure sensor portion 71, a sensor head cover 73 that covers the sensor base 72 and includes an opening 73a in a region opposite the pressure sensor portion 71, and a soft portion 74 provided in the opening 73a of the sensor head cover 73.

The sensor module 63 is disposed inside the movable case 61 and is supported by the movable case 61 in a manner allowing the sensor module 63 to move in a predetermined movement range in the direction of the ceiling and the opening of the movable case 61 opposing one another. In other words, the sensor module 63 is supported in a manner to be movable within the movable case 61, and the movement is restricted by a restriction portion such as a stopper or like when the sensor module 63 moves from the opening of the movable case 61 to the position where the sensor module 63 projects out a certain amount or more.

The pressure sensor portion 71 includes: a flexible substrate 71a, a substrate 71b mounted on the flexible substrate 71a, and a plurality of the pressure sensitive elements 71c mounted on the substrate 71b. The flexible substrate 71a is connected to the cable 15a and is electrically connected to the control board 15 via the cable 15a.

The substrate 71b and the plurality of pressure sensitive elements 71c constitute a sensor chip. The plurality of pressure sensitive elements 71c are arranged in one direction, forming a pressure sensitive element array 71d. A single or a plurality of the pressure sensitive element arrays 71d are provided. In the case in which the plurality of the pressure sensitive element arrays 71d are provided, the plurality of pressure sensitive element arrays 71d are disposed at predetermined intervals in a direction orthogonal to the arrangement direction of the plurality of pressure sensitive elements 71c.

Also, the pressure sensor portion 71 is disposed in the sensor base 72 such that the direction in which the plurality of pressure sensitive elements 71c are arranged is the width direction of the wrist 100. The pressure sensor portion 71 transmits a pressure value measured by the plurality of pressure sensitive elements 71c to the control board 15 via the cable 15a.

The sensor base 72 supports the pressure sensor portion 71 and the cable 15a connected to the pressure sensor portion 71. The sensor base 72 engages with the sensor head cover 73 on one main surface and supports the pressure sensor portion 71 in a region opposite the opening 73a of the sensor head cover 73. The movable base 64 is fixed on the other main surface of the sensor base 72.

The sensor head cover 73 comes into contact with the wrist 100 at an end surface. The soft portion 74 is provided in the opening 73a of the sensor head cover 73 and protects the pressure sensitive elements 71c. The opening 73a has a rectangular shape, for example.

The soft portion 74 is formed, for example, by injecting a relatively soft resin material such as a silicone resin into the opening 73a. An end surface of the soft portion 74 is formed flush with the end surface of the sensor head cover 73. Note that it is sufficient that the soft portion 74 comes into contact with the wrist 100 and is formed from a material that allows the pressure of the radial artery 110 to be detected by the pressure sensitive elements 71c, and the thickness, shape that comes into contact with the wrist 100, and material of the soft portion 74 can be selected as appropriate.

With the blood pressure measurement device 1 worn on the wrist 100, the movable base 64 is supported in the movable case 61 in a manner allowing the movable base 64 to move in a direction toward and a direction away from the wrist 100. For example, the movable base 64 is configured to move along the plurality of cylindrical members provided in the movable case 61, for example. The end portion of the movable base 64 on the wrist 100 side is fixed to the sensor base 72. Thus, the movable base 64 supports the sensor base 72 in a manner allowing the sensor base 72 to move in one direction with respect to the movable case 61. The movable base 64 includes a second support portion 64a that is provided on the outer surface of the movable base 64 and supports a portion of the biasing member 65.

The second support portion 64a supports a portion of the biasing member 65. The second support portion 64a is, for example, a cylindrical projection. The number of the second support portions 64a provided is the same as the number of biasing members 65 provided. As a specific example, the second support portion 64a is provided on the different outer surfaces of the movable base 64. For example, the second support portions 64a are provided on the outer surfaces of the side walls in a direction orthogonal to the circumferential direction of the wrist 100, specifically, the outer surfaces opposite the inner surfaces of opposite side walls of the movable case 61 provided with the first support portion 61c, when the sensor device 5 is worn on the wrist 100. Note that the positional relationship between the first support portion 61c and the second support portion 64a is set as appropriate by the shape and the like of the biasing member 65.

The biasing member 65 has a neutral state and generates a restoring force when an external force is applied while in the neutral state. As a specific example, the biasing member 65 is a torsion spring. A single or a plurality of the biasing members 65 are provided. For example, two biasing members 65 may be provided in point symmetrical positions about the center of the sensor unit 52 along the movement direction of the sensor module 63.

Both ends of the biasing member 65 are held by the first support portion 61c and the second support portion 64a. For example, both ends of the biasing member 65 have an annular shape or a hook-like shape and engage with the first support portion 61c and the second support portion 64a.

As illustrated in FIGS. 10 and 15, the biasing member 65 is in a neutral state in which a biasing force does not occur when an end of the sensor head cover 73 of the sensor module 63 is in a neutral point in a predetermined position with respect to the opening portion 41b of the attach portion 41. Here, the predetermined position is, for example, a position at which the end of the sensor module 63 projects from the opening portion 41b. As illustrated in FIGS. 11 and 16, the biasing member 65 biases the sensor module 63 in a direction toward the wrist 100 when the sensor module 63 is on the wrist 100 side of the neutral point. Also, as illustrated in FIGS. 9 and 14, the biasing member 65 biases the sensor module 63 in a direction away from the wrist 100 when the end of the sensor module 63 is at a position separated from the wrist 100 further than the neutral point.

As illustrated in FIG. 19, the adjustment portion 53 is configured to adjust the position of the sensor unit 52, with respect to the case 51, in the circumferential direction of the wrist 100. The adjustment portion 53 is located on the outer surface of the case 51 and includes an adjustment catch 53a, the portion of which is fixed to the fixing portion 61b of the movable case 61 via the third hole portion 51e. Also, the adjustment portion 53 includes: graduations 53b provided adjacent to the third hole portion 51e of the case 51 and an instruction portion 53c provided on the adjustment catch 53a that indicates the graduations 53b.

The adjustment catch 53a is connected to the sensor unit 52 by being fixed to the movable case 61. The adjustment catch 53a is configured to move the sensor unit 52. In other words, the adjustment portion 53 is an adjustment mechanism that, by the adjustment catch 53a being moved in the longitudinal direction of the third hole portion 51e, moves the sensor unit 52 along the second groove 51f2 and adjusts the position of the sensor unit 52 with respect to the case 51.

The graduations 53b and the instruction portion 53c are display portions that display the position of the adjustment catch 53a, i.e., the position of the sensor unit 52 connected to the adjustment catch 53a, in a visually recognizable manner.

The fastener 43 includes, for example, one or a plurality of band-like bands and a fixing member such as a hook-and-loop fastener that secures the band wrapped around the wrist 100. The fastener 43 fixes the attach portion 41 and the sensing body 42 to the wrist 100. Note that the fastener 43 may be composed of: a first belt referred to as a parent that includes a buckle; and a second belt referred to as a pointed end that is fixed to the buckle. Also, the fastener 43 may further have a configuration in which the case 51 is fixed to the attach portion 41 by the fastener 43 being wrapped around the case 51.

In other words, the fastener 43 is configured to prevent the case 51 from moving in a direction away from the attach portion 41 when the reaction force, when the sensor module 63 presses against the wrist 100 due to the expansion of the air bag 62, acts on the movable case 61 and when the case 51 is directly pressed by the movable case 61 or indirectly pressed via the adjustment catch 53a from the movable case 61.

Next, an example of measurement of a blood pressure value using the blood pressure measurement device 1 will be described using FIGS. 20 to 23. FIG. 20 is a flowchart illustrating an example of a blood pressure measurement using the blood pressure measurement device 1, illustrating both the operation of the user and the operation of the control unit 33. FIGS. 21 to 23 are explanatory diagrams illustrating an example of blood pressure measurement using the blood pressure measurement device 1.

First, the user searches by palpation for the position of the radial artery 110 of the wrist 100 (step ST1). For example, at this time, a visible line may be drawn on the skin above the radial artery 110 with a pen.

The user then separates the sensing body 42 of the sensor device 5 from the attach portion 41. In the present embodiment, the user operates the engagement portion 51b to release the engagement of the case 51 with the base portion 41a and rotates the sensing body 42 about the rotation shaft 51a in a direction away from the attach portion 41.

The user then attaches the device body 4 and the sensor device 5 as illustrated in FIG. 21 (step ST2). As a specific example, the user first passes the wrist 100 through the body fastener 16 of the device body 4 and the fastener 43 of the sensor device 5 and places the device body 4 and the sensor device 5 at a predetermined position on the wrist 100. Next, the user tightens the body fastener 16 of the device body 4 and fixes the device body 4 to the wrist 100. Here, in a case of configuration in which a cuff is provided on the body fastener 16 of the device body 4, the user checks to see whether the skin of the wrist 100 is caught in the body fastener 16 (cuff) and whether the body fastener 16 (cuff) is too loose. Next, the user adjusts the position of the sensor device 5 so that the opening portion 41b of the attach portion 41 of the sensor device 5 is located at the radial artery 110 of the wrist 100. In addition, the user tightens the fastener 43 of the sensor device 5, and the sensor device 5 is fixed to the wrist 100, with the radial artery 110 held at the position of the opening portion 41b.

Next, as illustrated in FIG. 22, the user palpates the wrist 100 from the opening portion 41b of the attach portion 41 (step ST3) and checks again that the radial artery 110 is located at the opening portion 41b. Then, as illustrated in FIG. 23, the user rotates the sensing body 42 in a direction toward the attach portion 41 and fixes the sensing body 42 to the attach portion 41 via the engagement portion 51b. Note that when the position of the sensing body 42 is misaligned with the radial artery 110, the user operates the adjustment catch 53a and adjusts the position of the sensing body 42.

Note that at this time, the biasing member 65 biases the sensor module 63 away from the wrist 100, and as illustrated in FIG. 14, the sensor module 63 is located at a position separated from the wrist 100 further than the neutral point and located closer to the case 51 than the opening portion 41b. Thus, as illustrated in FIG. 14, the sensor head cover 73 of the sensor module 63 is separated away from the wrist 100.

Next, the user operates the operation portion 12 to send an instruction to measure the blood pressure. The control unit 33 measures the blood pressure on the basis of the blood pressure measurement instruction (step ST4). At this time, the control unit 33 drives and controls the pump 14, and, as illustrated in FIGS. 10 and 15, the air bag 62 is expanded, moving the sensor module 63 progressively toward the wrist 100 from a state of being housed inside the movable case 61 as illustrated in FIGS. 9 and 14. Thus, as illustrated in FIGS. 11 and 16, the sensor head cover 73 and soft portion 74 of the sensor module 63 press against the region in which the radial artery 110 of the wrist 100 is found.

At this time, the sensor module 63 moves beyond the neutral point illustrated in FIG. 15 toward the wrist 100 as illustrated in FIG. 16. One end of the biasing member 65 is rotatably supported by the first support portion 61c, and the movable case 61 is fixed against the wrist 100. Thus, the biasing member 65 rotates about the first support portion 61c as the sensor module 63 moves, moving from the orientation of the upper diagram in FIG. 12 (FIG. 9), through the orientation of the middle diagram in FIG. 12 (FIG. 10), to the orientation of the lower diagram of FIG. 12 (FIG. 11). This causes the biasing member 65 to bias the sensor module 63 in a direction toward the wrist 100 due to a change in the direction of bias, passing through the neutral state when the sensor module 63 moves beyond the neutral point. As a result, the sensor module 63 presses against the wrist 100 due to the force applied by the air bag 62 and the biasing member 65.

In this way, by pressing the sensor head cover 73 and the soft portion 74 against this region of the wrist 100, the radial artery 110 is pressed with an appropriate amount of pressure so that a flat portion is formed in the radial artery 110, as illustrated in FIG. 16. In this state, the pressure sensitive elements 71c of the pressure sensor portion 71 measure the pressure pulse waves.

Note that the control unit 33 obtains the blood pressure via the tonometry method from the pressure pulse waves of the radial artery 110 detected by the pressure sensor portion 71. Note that prior to blood pressure measurement, the control unit 33 may perform a blood pressure measurement for calibration on the basis of program data stored in the storage unit 32 or may perform a check to determine whether or not the worn state of the device body 4 and/or the sensor device 5 and the position of the pressure sensor portion 71 are correct.

According to the blood pressure measurement device 1 configured in this manner, the biasing member 65 biases the sensor module 63 in a direction away from the wrist 100 with force along one direction when the sensor head cover 73 is positioned further away from the wrist 100 than the neutral point.

With this configuration, in the blood pressure measurement device 1, after blood pressure measurement, the sensor module 63 moves to the neutral point due to a reaction force from the wrist 100, and then the sensor module 63 is biased by the biasing member 65 and moves from the neutral point until the sensor module 63 is housed in the movable case 61.

This causes the sensor module 63 to be located in the movable case 61 more so than in the opening 41b, and when the worn blood pressure measurement device 1 is removed, the sensor module 63 of the sensor device 5 does not project outward.

As a result, the sensor module 63 does not interfere with the wrist 100 and other configurations, and thus the wrist 100 is not burdened. Also, damage caused by interference with other configurations can be prevented. In addition, by the biasing member 65, being biased in the direction of housing within the movable case 61, the sensor module 63 is configured to move back and forth in one direction relative to the movable case 61 by the air bag 62 and the biasing member 65.

Also, according to the blood pressure measurement device 1, the neutral point is configured to be located where the end of the sensor module 63 projects from the opening 41b. With this configuration, after the end of the blood pressure measurement, the blood pressure measurement device 1 can use the reaction force from the wrist 100 to move the sensor module 63 to a position separated from the wrist 100 further than the neutral point. Thus, the biasing direction of the biasing member 65 can be easily switched from the direction of pressing the sensor module 63 toward the wrist to a direction of biasing the sensor module 63 away from the wrist 100.

Also, according to the blood pressure measurement device 1, the biasing member 65 is configured to bias the sensor module 63 in a direction toward the wrist 100 with force along one direction, with the neutral point of the sensor module 63 acting as the boundary, when the sensor head cover 73 is positioned closer to the wrist 100 than the neutral point. According to this configuration, when the blood pressure measurement device 1 is used for blood pressure measurement, the air bag 62 and the biasing member 65 press the sensor module 63 toward the wrist 100, allowing the sensor head cover 73 to be suitably pressed against the wrist 100.

As a specific example, a relationship between stroke (mm) and pressing force (N) of a Comparative Example including the air bag 62 and no biasing member 65 and an Example including the air bag 62 and the biasing member 65 will be described using FIG. 24. Note that the configurations other than the presence or absence of the biasing member 65 are the same in both the Example and the Comparative Example, and each of the blood pressure measurement devices 1 controls the pump 14 so that the pressure inside the air bag 62 is 250 mmHg. Also, the 0 mm stroke position is where the air bag 62 is not inflated and the sensor module 63 is in a position separated from the wrist 100 further than the neutral point. The term stroke is the amount of movement of the sensor module 63 from that position.

As illustrated in FIG. 24, the blood pressure measurement device of the Comparative Example does not include the biasing member 65. Thus, the pressing force progressively decreases as the stroke increases. This is because when the air bag 62 expands, the side surface of the air bag 62 in the direction orthogonal to the expansion direction also expands. In contrast, as illustrated in FIG. 24, with the blood pressure measurement device 1 of the Example, the biasing force caused by the biasing member 65 increases as the stroke increases. In this way, the biasing member 65 compensates for a decrease in the pressing force caused by expansion of the air bag 62, and the pressing force can be made substantially constant. As a result, the blood pressure measurement device 1 can prevent a decrease in the pressing force when the stroke increases.

Furthermore, FIG. 25 illustrates the relationship between stroke and pressing force for Example 1, Example 2, and Example 3 in which the target value of the internal pressure of the air bag 62 is set to 250 mmHg, 200 mmHg, and 150 mmHg, respectively. As can be seen from FIG. 25, by providing the biasing member 65, the blood pressure measurement device 1 achieves the same effect regardless of the target value of the internal pressure of the air bag 62. In other words, as in Example 1 to Example 3, while there is a difference in pressing force due to the different target values of the internal pressure of the air bag 62, the pressing force can be made substantially constant with respect to the stroke by providing the biasing member 65.

In addition, by setting the biasing member 65, the blood pressure measurement device 1 can increase the pressing force, when the stroke increases, by the air bag 62 and the biasing member 65, which constitute the pressing mechanism, and can set the pressing force to maximum when pressing the wrist 100.

In addition, because the blood pressure measurement device 1 can set the force pressing the wrist 100 to a preferred force with a simple configuration in which the biasing member 65 is provided, it is not necessary to increase the capacity of the pump 14 or complicate the control of the pump 14. In addition, in the blood pressure measurement device 1, because the sensor module 63 can press the wrist 100 with an appropriate pressing force, a flat portion can be suitably made in the radial artery 110, and the accuracy of the blood pressure measurement can be improved.

Also, the blood pressure measurement device 1 has a simple configuration in which the sensor module 63 can be biased with the bias member 65 being a torsion spring. Thus, an increase in manufacturing cost can be prevented. Furthermore, because a plurality of the biasing members 65 are provided, the size of each of the plurality of biasing members 65 needed to create a desired biasing force can be made small and used as such, compared to a configuration in which a single biasing member is provided. Thus, the sensor device 5 can keep the space and configuration small for installing and supporting the biasing members 65.

In addition, the sensor device 5 includes a pair of the biasing members 65 disposed with point symmetry on either side of the sensor module 63. Thus, the sensor device 5 can uniformly apply a biasing force to the sensor module 63. This allows the sensor device 5 to stably move the sensor module 63 because the biasing force of the bias member 65 applied thereto moves along one direction. That is, by applying a biasing force to a portion of the sensor module 63, a force in a direction other than the movement direction of the sensor module 63 may be applied to the sensor module 63. However, with the present configuration, a biasing force along the movement direction of the sensor module 63 can be applied to the sensor module 63.

Also, the blood pressure measurement device 1 can be configured to bias the sensor module 63 by the biasing member 65 to move the sensor module 63 back and forth in one direction with a simple configuration. In other words, the wrist 100 can be palpated from the opening portion 41b, and, when the sensor device 5 of the blood pressure measurement device 1 is worn on the wrist 100, the sensor device 5 is worn in an ad-lib state on the wrist 100 and the radial artery 110 is found by palpation; thereafter, the sensor device 5 is adjusted in position and worn properly. As a result, the blood pressure measurement device 1 can be easily worn at the appropriate position.

In addition, because the sensor device 5 has a configuration that includes the adjustment portion 53, the adjustment catch 53a can be operated even after the sensor device 5 is worn properly on the wrist 100. This allows the position of the sensor unit 52 with respect to the radial artery 110 to be adjusted, which further allows the pressure of the radial artery 110 to be measured at a suitable position.

Furthermore, the sensor device 5 has a configuration in which the sensing body 42 is configured to be moved in a direction away from the attach portion 41 and in which the sensing body 42 rotates away from the attach portion 41 about an axis. Thus, when the sensing body 42 is moved, the sensor module 63 provided on the sensing body 42 moves in a direction away from the opening portion 41b of the attach portion 41.

This can prevent the sensor module 63 from moving while in contact with the wrist 100 and the attach portion 41 when the sensing body 42 is moved with respect to the attach portion 41. Specifically, the sensor unit 52 measures the blood pressure, with the sensor head cover 73 and the soft portion 74 of the sensor module 63 projecting from the opening of the movable case 61, at a position where the wrist 100 can be appropriately pressed via the air bag 62.

Even when the sensing body 42 is moved with respect to the attach portion 41 in this state, in the sensing body 42, the sensor module 63 moves in a direction away from the wrist 100. Thus, the sensing body 42 cannot move in a state of the end surface of the sensor head cover 73 and the soft portion 74 being in contact with the wrist 100 or the attach portion 41. As a result, when the sensing body 42 is moved, damage caused by the sensor module 63 interfering other configurations or the wrist 100 and a load on the wrist 100 can be prevented.

In this way, because the sensor device 5 is provided with the opening portion 41b with a shape that allows palpation through the attach portion 41 and the sensing body 42 is configured to move in a direction away from the attach portion 41 and the wrist 100, damage to the sensor module 63 can be prevented and safety can be improved.

Also, the sensor device 5 has a configuration in which the sensing body 42 rotates with respect to the attach portion 41 at one end side in the longitudinal direction of the attach portion 41. Thus, substantially the entire region of the upper surface of the attach portion 41 can be exposed to the outside. As a result, the opening portion 41b of the attach portion 41 is completely exposed, allowing the size of the shape of the opening portion 41b required for palpation to be kept as small as possible. Furthermore, in the sensor device 5, a rail configuration for sliding the sensing body 42 with respect to the attach portion 41; or a configuration for supporting the sensing body 42 on the attach portion 41 after sliding are not necessary. Thus, the shape in the width direction of the wrist 100 of the sensor device 5 can be kept as small as possible. This allows the sensor device 5 to be made compact.

As described above, according to the blood pressure measurement device 1 according to an embodiment of the present invention, the attach portion 41 is provided with the opening 41b having a shape that allows for palpation, and the sensing body 42 that rotates about a single axis with respect to the attach portion 41 is provided. This allows palpation of the wrist when the device is worn and can prevent the sensor module 63 from being damaged.

Note that the present invention is not limited to the embodiment described above. The biasing member 65 is not limited to being a torsion spring and may be composed of a different elastic body. The biasing member 65 is only required to have a configuration that is able to elastically deform due to an external force in one direction and to restore its shape in a direction opposite to the direction the external force is applied. For example, as illustrated in FIG. 26, the biasing member 65 may be formed from a resin material and be configured to bias the sensor module 63 using a so-called rubber-switch-shaped elastic body. When the biasing member 65 is formed from a resin material in this manner, the resin material can have various shapes depending on the molding die. Thus, the options for the positions and shapes that can be disposed between the movable case 61 and the sensor module 63 are increased, so the design has a high degree of freedom, forming can be performed with a mold, and manufacturing is made easy.

Also, in the example described above, the biasing member 65 describes a configuration in which a different bias force is applied to the sensor module 63, with the neutral point of the sensor module 63 acting as the boundary. However, no such limitation is intended. For example, the biasing member 65 may be configured such that the sensor module 63 is separated from the wrist 100 and biases the sensor module 63 only in the direction in which the sensor module 63 is housed in the movable case 61. This configuration may allow the sensor module 63 to be pressed by the air bag 62 when the wrist 100 is pressed by the sensor head cover 73 and may allow the sensor module 63 to be biased by the biasing member 65 when housed. Similarly, the biasing member 65 may be configured as a part of the pressing mechanism, with the air bag 62, that is configured to bias the sensor module 63 when pressing the wrist 100.

Also, in the example described above, the blood pressure measurement device 1 has a configuration in which the device body 4 and the sensor device 5 are different bodies. However, no such limitation is intended. For example, as illustrated in FIGS. 27 and 28, the blood pressure measurement device 1 may have a configuration in which the device body 4 and the sensor device 5 are integrally formed. The blood pressure measurement device 1 with such a configuration, for example, may have configuration in which the operation portion 12, the display portion 13, the pump 14, and the control board 15 used in the device body 4 are provided in the case 51 of the sensing body 42.

Also, in the example described above, the blood pressure measurement device 1 has a configuration in which the sensing body 42 moves in a direction away and a direction toward the attach portion 41 by the sensing body 42 rotating with respect to the attach portion 41 about an axis. However, no such limitation is intended. For example, as illustrated in FIG. 29, the blood pressure measurement device 1 may have a configuration in which the sensing body 42 moves in a direction away and a direction toward the attach portion 41 by the attach portion 41 and the sensing body 42 being separated. In the case in which the blood pressure measurement device 1 has this configuration, the engagement portions 51b are provided at a plurality of positions on the case 51 of the sensing body 42, and the sensing body 42 engages with the attach portion 41 at these positions.

Also, in the examples described above, the blood pressure measurement device 1 has a configuration that measures the pressure of the radial artery 110 and that obtains the blood pressure by the tonometry method. However, no such limitation is intended. In another example, the pressure of the ulnar artery 112 is measured. The blood pressure measurement device 1 may also have a configuration in which the blood pressure is obtains via a method other than the tonometry method. In other words, the blood pressure measurement device 1 is only required to have a configuration in which the sensor module 63 that comes into contact with the wrist 100 is capable of moving with respect to the opening portion 41b of the attach portion 41 and the wrist 100. In addition, similarly, the present invention is not limited to a device for measuring blood pressure and may be applied to other devices using other measurement methods such as devices for measuring pulse waves.

In the examples described above, a configuration is described in which the opening portion 41b of the attach portion 41 has a shape that allows for palpation of the wrist 100. However, no such limitation is intended. That is, as long as the opening portion 41b of the attach portion 41 has a shape that allows the sensor unit 52 to come into contact with wrist 100 beyond the opening portion 41b, in a range in which position is adjusted by the adjustment portion 53, a shape that does not allow palpation of the wrist 100 may be used.

Also, in the example described above, the sensor unit 52 has a configuration in which the sensor base 72 of the sensor module 63 is supported by the movable base 64 in a manner allowing the sensor base 72 to move within the movable case 61. However, no such limitation is intended. For example, the movable base 64 may be integrally formed with the sensor base 72 of the sensor module 63.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

Note that the present invention is not limited to the embodiments described above, various embodiments and modifications within the spirit of invention are possible. Furthermore, each of the embodiments may be combined as appropriate to obtain the combined effects of the embodiments. Also, the embodiments described above include various stages of invention, and various inventions may be obtained by appropriately combining the multiple configuration requirements disclosed.

REFERENCE SIGNS LIST

1 Blood pressure measurement device
4 Device body
5 Sensor device
11 Body case
12 Operation portion
13 Display portion
14 Pump
14*a* Tube
15 Control board
15*a* Cable
16 Body fastener
21 Button
31 Communication unit
32 Storage unit
33 Control unit
41 Attach portion
41*a* Base portion
41*b* Opening portion
41*c* Attachment portion
41*d* Cushion
42 Sensing body
43 Fastener
51 Case
51*a* Rotation shaft
51*b* Engagement portion
51*c* First hole portion
51*d* Second hole portion
51*e* Third hole portion
51*f* Guide groove
51/1 First groove
51/2 Second groove
52 Sensor unit
53 Adjustment portion
53*b* Graduations
53*c* Instruction portion
61 Movable case (case)
61*a* Guide projection
61*b* Fixing portion
61*c* First support portion
62 Air bag
63 Sensor module
64 Movable base
64*a* Second support portion
65 Biasing member
71 Pressure sensor portion
71*a* Flexible substrate
71*b* Substrate
71*c* Pressure sensitive element
71*d* Pressure sensitive element array
72 Sensor base
73 Sensor head cover
73*a* Opening
74 Soft portion
100 Wrist
110 Radial artery
111 Radius
112 Ulnar artery
113 Ulna
114 Tendon

The invention claimed is:

1. A blood pressure measurement device comprising:
an attach portion including:
an opening provided at a position opposite a region where one artery of a wrist is found; and
an end surface that curves conforming to a shape in a circumferential direction of a portion of the wrist;
a fastener provided on the attach portion; and
a sensing body including:
a sensor unit disposed opposite the opening, the sensor unit including a sensor that comes into contact with the region where the one artery of the wrist is found and an air bag that presses the sensor toward the wrist by expanding when the blood pressure measurement device is worn on the wrist;
a case that houses the sensor in a manner allowing the sensor to move in one direction with respect to the opening, and
an elastic body that biases the sensor with respect to the wrist,
wherein the elastic body:
biases the sensor in a direction toward the wrist when an end of the sensor is located on a side of the wrist from a neutral point, the neutral point being a predetermined position respect to; and
biases the sensor in a direction away from the wrist when the end of the sensor is located at a position further away from the wrist than the neutral point.

2. The blood pressure measurement device according to claim 1, wherein
the neutral point is a position where the end of the sensor projects from the opening.

3. The blood pressure measurement device according to claim 1, wherein
the elastic body is a torsion spring.

4. The blood pressure measurement device according to claim 3, wherein
a plurality of the torsion springs are provided.

5. The blood pressure measurement device according to claim 4, wherein
two of the torsion springs are provided on either side of the sensor in a direction orthogonal to the circumferential direction of the wrist when the blood pressure measurement device is worn on the wrist, and
one end of each of the torsion springs is fixed to the sensor and an other end of each of the torsion springs is fixed to the case.

6. The blood pressure measurement device according to claim 1, wherein the elastic body is formed from a resin material and deforms due to an external force in one direction and restores its shape in a direction opposite to the direction in which the external force is applied.

7. The blood pressure measurement device according to claim 2, wherein the elastic body is a torsion spring.

8. The blood pressure measurement device according to claim 2, wherein the elastic body is formed from a resin material and deforms due to an external force in one direction and restores its shape in a direction opposite to the direction in which the external force is applied.

\* \* \* \* \*